(12) United States Patent
Boyanov

(10) Patent No.: US 10,551,342 B2
(45) Date of Patent: Feb. 4, 2020

(54) FIELD EFFECT SENSORS

(71) Applicant: ILLUMINA, INC., San Diego, CA (US)

(72) Inventor: Boyan Boyanov, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 16/024,299

(22) Filed: Jun. 29, 2018

(65) Prior Publication Data

US 2019/0041354 A1 Feb. 7, 2019

Related U.S. Application Data

(60) Provisional application No. 62/539,813, filed on Aug. 1, 2017.

(51) Int. Cl.
*H01L 21/02* (2006.01)
*G01N 27/414* (2006.01)
(Continued)

(52) U.S. Cl.
CPC ....... *G01N 27/4145* (2013.01); *C12Q 1/6869* (2013.01); *G01N 27/4146* (2013.01);
(Continued)

(58) Field of Classification Search
CPC ... H01L 21/02; H01L 21/0259; H01L 21/762; H01L 21/76216; H01L 21/76218;
(Continued)

(56) References Cited

U.S. PATENT DOCUMENTS

2007/0231790 A1 10/2007 Su
2007/0264634 A1 11/2007 Bock et al.
(Continued)

FOREIGN PATENT DOCUMENTS

WO 2017/098518 6/2007
WO 2016/161246 10/2016

OTHER PUBLICATIONS

Kulkarni, G. , et al., "Detection beyond the Debye Screening Length in a High-Frequency Nanoelectronic Biosensor," Nano Letters, 12:719-723, Jan. 3, 2012.
(Continued)

*Primary Examiner* — Chuong A Luu
(74) *Attorney, Agent, or Firm* — Illumina, Inc.

(57) ABSTRACT

Apparatus and methods are disclosed for single molecule field effect sensors having conductive channels functionalized with a single active moiety. A region of a nanostructure (e.g., such as a silicon nanowire or a carbon nanotube) provide the conductive channel. Trapped state density of the nanostructure is modified for a portion of the nanostructure in proximity with a location where the active moiety is linked to the nanostructure. In one example, the semiconductor device includes a source, a drain, a channel including a nanostructure having a modified portion with an increased trap state density, the modified portion being further functionalized with an active moiety. A gate terminal is in electrical communication with the nanostructure. As a varying electrical signal is applied to an ionic solution in contact with the nanostructure channel, changes in current observed from the semiconductor device can be used to identify composition of the analyte.

26 Claims, 18 Drawing Sheets

(51) Int. Cl.
   *C12Q 1/6869* (2018.01)
   *G01R 19/00* (2006.01)
   *H03K 3/03* (2006.01)

(52) U.S. Cl.
   CPC ...... *H01L 21/0259* (2013.01); *G01R 19/0092* (2013.01); *H03K 3/0315* (2013.01)

(58) Field of Classification Search
   CPC ....... H01L 21/76237; H01L 21/823412; H01L 21/823487; H01L 21/823885; H01L 29/66439; H01L 29/775; H01L 31/113; H01L 31/0352; H01L 31/1136; H01L 31/035218; G01N 27/414; G01N 27/4145; G01N 27/4146
   USPC ......................................................... 257/253
   See application file for complete search history.

(56) References Cited

U.S. PATENT DOCUMENTS

2013/0115705 A1    5/2013   Patolsky et al.
2015/0093849 A1    4/2015   Shepard et al.
2015/0226699 A1    8/2015   Li et al.
2018/0372678 A1*  12/2018   Patolsky ................ B82Y 15/00

OTHER PUBLICATIONS

International Search Report and Written Opinion in PCT/US2018/040439 dated Nov. 15, 2018, 16 pages.

* cited by examiner

FIELD EFFECT SENSORS

CROSS-REFERENCE TO RELATED APPLICATIONS

This application claims priority to U.S. Provisional Patent Application No. 62/539,813, filed Aug. 1, 2017, the contents of which is incorporated by reference herein in its entirety.

BACKGROUND

Field effect transistors can be used as single-molecule charge sensors to identify molecules. Such sensors may be operated at biologically relevant salt conditions. The Debye screening length of such salt solutions is in the range of about 0.3 nm to about 10 nm, which limits the sensing zone to a few nanometers outside the surface of the channel and often reduces signal levels to the limit of detectability. A work-around to this difficulty is to perform the biological reaction and the measurements in two different buffers—high salt and low salt, respectively. However, such an approach is not typically suitable for single-molecule sensors where buffer exchange is not possible.

SUMMARY

In a first aspect, a semiconductor device comprises a source; a drain; a channel comprising a nanostructure, the nanostructure comprising a modified portion having an increased trap state density, the modified portion being functionalized with an active moiety; and a gate terminal in electrical communication with the nanostructure.

In an example, the nanostructure comprises at least one of: a nanowire, a nanotube, and a nanoribbon.

In another example, the nanostructure comprises at least one of: a silicon nanowire, a carbon nanotube, a polymer nanowire, a graphene nanoribbon, and a $MoS_2$ nanoribbon.

In still another example, the nanostructure comprises at least one of: graphene, silicene, and phosphorene.

In an example, the modified portion is formed by ion implantation, energetic beam irradiation, plasma exposure, or a combination thereof.

In an example, the active moiety comprises an enzyme or an aptamer that is linked to the modified portion of the nanostructure; and linkage of the enzyme or the aptamer to the modified portion of the nanostructure disrupts atomic bonds of the nanostructure to increase the trap state density of the modified portion of the nanostructure. In some instances of this example, the linked enzyme or aptamer is covalently bonded to the modified portion of the nanostructure.

In an example, the active moiety is a single molecule of one of the following: a single enzyme, a single antibody, and a single aptamer.

In an example, the increased trap state density is in a range of about $1 \times 10^{-12}$ traps/cm$^2$ to about $1 \times 10^{-14}$ traps/cm$^2$.

It is to be understood that any features of this first aspect may be combined together in any desirable manner and/or configuration.

In a second aspect, an apparatus comprises the semiconductor device of claim 1; and a vessel at least partially enclosing the nanostructure, the vessel to receive an analyte solution providing the electrical communication between the gate terminal and the nanostructure.

In a third aspect, an apparatus comprises the semiconductor device of claim 1, wherein the semiconductor device further comprises a body terminal coupled to a modulated signal input; and the gate terminal is coupled to a fixed voltage.

In a fourth aspect, an apparatus comprises a current sensor or ring oscillator, the current sensor or ring oscillator comprising the semiconductor device of claim 1.

It is to be understood that any combination of features of the semiconductor device may be used with any of the second, third, or fourth aspects. Moreover, it is to be understood that any features of any of the apparatus of the second, third, or fourth aspect may be used together, and/or that any features from any of these may be combined with any of the examples disclosed herein.

In a fifth aspect, a method of manufacturing comprises depositing a nanostructure over a substrate having at least one source region and at least one drain region within or over the substrate to form an electrically conductive channel between the source region and the drain region, the nanostructure having an increased trap state density for a portion but not all of the nanostructure; and linking an active moiety to the nanostructure portion.

An example of the method further comprises generating the increased trap state density by covalently linking the active moiety to the nanostructure portion.

Another example of the method further comprises generating the increased trap state density by implanting ions to the nanostructure portion.

Still another example of the method further comprises generating the increased trap state density by performing localized doping of the nanostructure portion.

Yet another example of the method further comprises increasing the trap state density of the nanostructure portion by adjusting a composition of a source material in a chemical vapor deposition process when depositing the nanostructure over the substrate.

In an example, the nanostructure comprises at least one of: a nanowire, a nanotube, and a nanoribbon.

In another example, the nanostructure comprises at least one of: a silicon nanowire, a carbon nanotube, a polymer nanowire, a graphene nanoribbon, and a $MoS_2$ nanoribbon.

In yet another example, the nanostructure comprises at least one of: graphene, silicene, and phosphorene.

An example of the method further comprises selecting: a desired $\Delta C_{ox}$ parameter, or a desired drain current to gate voltage response, or the desired $\Delta C_{ox}$ parameter and the desired drain current to gate voltage response; selecting a desired trap state density for the nanostructure portion; and increasing the trap state density according to the selected desired trap state density.

An example of the method further comprises selecting at least one of a material and a dosage for the nanostructure portion according to the selected desired trap state density.

It is to be understood that any features of the fifth aspect may be combined together in any desirable manner. Moreover, it is to be understood that any combination of features of the first aspect, and/or of the second aspect, and/or of the third aspect, and/or of the fourth aspect, and/or of the fifth aspect may be used together, and/or that any features from any of these may be combined with any of the examples disclosed herein.

In a sixth aspect, a method of using a semiconductor device comprises linking an enzyme to a channel of a field effect transistor in proximity to a sensing zone, the field effect transistor having a source terminal, a drain terminal, and a nanostructure forming a channel between the source terminal and the drain terminal, the sensing zone comprising a region of relatively higher trap state density on the nanostructure; providing an ionic solution in proximity with the sensing zone; applying a signal to a terminal of the field effect transistor; and detecting changes in current flow through the field effect transistor responsive to the applied signal.

In an example, the signal is modulated at a frequency exceeding a plasma frequency of the solution.

In an example, the solution has a salinity ranging from about 1 millimolar (mM) to about 500 millimolar (mM).

In an example, the signal is provided to a gate terminal or a body terminal of the field effect transistor.

In an example, the detecting of changes in current flow comprises detecting a phase change of an output signal of the field effect transistor relative to the signal applied to the terminal.

An example of this method further comprises sequencing a series of nucleotides in a deoxyribonucleic acid (DNA) or ribonucleic acid (RNA) molecule based on the detected changes.

It is to be understood that any features of the sixth aspect may be combined together in any desirable manner. Moreover, it is to be understood that any combination of features of the first aspect, and/or of the second aspect, and/or of the third aspect, and/or of the fourth aspect, and/or of the fifth aspect, and/or of the sixth aspect may be used together, and/or that any features from any of these may be combined with any of the examples disclosed herein.

Still further, it is to be understood that any features of any of the aspects may be combined together in any desirable manner, and/or may be combined with any of the examples disclosed herein.

DETAILED DESCRIPTION

I. General Considerations

Figure 1A:
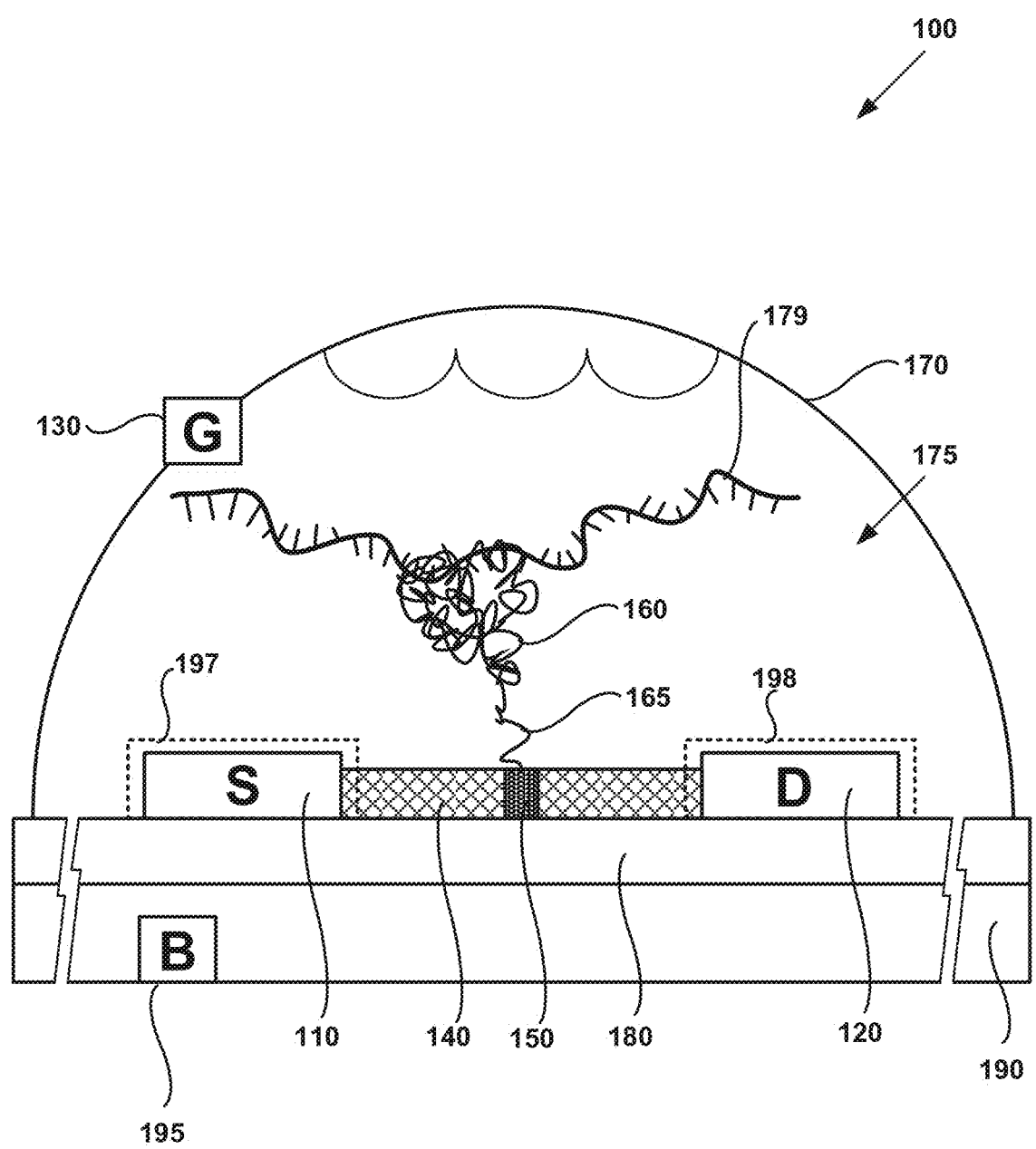
FIGS. 1A and 1B are schematic representations of a generalized example field-effect sensor, as can be used in certain examples of the technology disclosed herein.

Disclosed herein are representative examples of methods, apparatus, and systems for the design, manufacture, and use of semiconductor devices having nanostructure channels (e.g., channels implemented with nanowires, nanotubes, nanoribbons, or other geometries with critical dimensions smaller than about 100 nm), including semiconductor devices where the nanostructure channel has a modified portion having an adjusted trap state density in or near a location where an active moiety is linked to the nanostructure. The methods, apparatus, and systems are related generally to biosensor-based detection, including, for example, biosensors that can be used for nucleic acid sequencing.

As used herein, a "nanowire" is a structure with a solid cylindrical shape having a width smaller than about 100 nm, and a length that can be significantly longer than the width. Electrical conduction occurs through the entire volume of the nanowire. As used herein, a "nanotube" is a structure with a hollow cylindrical shape having a width smaller than about 100 nm and a length that can be significantly longer than the width. In some examples, a nanotube is a single sheet or ribbon of graphene wrapped into a cylindrical shape. The cylinder is hollow in the middle and electrical conduction occurs through the tubular sidewall of the cylinder. As used herein, a "nanoribbon" is a structure with a flat shape having a width smaller than about 100 nm and a length that may be either similar to or significantly longer than the width. The thickness of the nanoribbon corresponds to the material from which it is made. Single-layer graphene nanoribbons have a thickness ranging from about 0.3 nm to about 0.4 nm. Electrical conduction occurs through the entire volume of the nanoribbon. Unless stated otherwise, "semiconductor" as used herein includes materials such as silicon (Si), germanium (Ge), silicon carbide (SiC), gallium nitride (GaN), gallium arsenide (GaAs), indium arsenide (InAs) as well as materials that behave as semiconductors when arranged in a nanostructure, for example, carbon nanotubes, boron nitride nanotubes, or other semiconducting nanostructures.

The methods, apparatus, and systems disclosed herein should not be construed as being limiting in any way. Instead, the present disclosure is directed toward all novel and nonobvious features and aspects of the various disclosed examples, alone and in various combinations and subcombinations with one another. The disclosed methods, apparatus, and systems are not limited to any specific aspect or feature or combination thereof, nor do the disclosed examples require that any one or more specific advantages be present or problems be solved.

Although the operations of some of the methods disclosed herein are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the systems, methods, and apparatus can be used in conjunction with other things and methods. Additionally, the description sometimes uses terms like "produce," "generate," "select," "receive," "link," and "provide" to describe the methods disclosed herein. These terms are high-level descriptions of the actual operations that are performed. The actual operations that correspond to these terms may vary depending on the particular implementation, and are readily discernible by one of ordinary skill in the art having the benefit of the present disclosure.

As used in this application and in the claims, the singular forms "a," "an," and "the" include the plural forms unless the context clearly dictates otherwise. Additionally, the term "includes" means "comprises." Moreover, unless the context dictates otherwise, the term "coupled" means mechanically, electrically, or electromagnetically connected or linked and includes both direct connections or direct links and indirect connections or indirect links through one or more intermediate elements not affecting the intended operation of the described system.

It is to be understood that the ranges provided herein include the stated range and any value or sub-range within the stated range, as if such values or sub-ranges were explicitly recited. For example, a range from about 10 KHz to about 100 KHz should be interpreted to include not only the explicitly recited limits of from about 10 KHz to about 100 KHz, but also to include individual values, such as about 78 KHz, about 94.5 KHz, etc., and sub-ranges, such as from about 25 KHz to about 85 KHz, from about 15 KHz to about 80 KHz, etc.

The terms "substantially" and "about" used throughout this specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, or such as less than or equal to ±0.05%.

Additionally, certain terms may be used, such as "up," "down," "upper," "lower," and the like. These terms are used, where applicable, to provide some clarity of description when dealing with relative relationships. However, these terms are not intended to imply absolute relationships, positions, and/or orientations.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

Any of the computer-implemented methods disclosed herein can be implemented using computer-executable instructions stored on one or more computer-readable media (e.g., computer-readable media, such as one or more optical media discs, volatile memory components (such as DRAM or SRAM), or nonvolatile memory components (such as flash memory or hard drives)) and executed on a computer (e.g., any commercially available computer, including smart phones or other mobile devices that include computing hardware). Any of the computer-executable instructions for implementing the techniques disclosed herein, as well as any data created and used during such implementation, can be stored on one or more computer-readable media (e.g., computer-readable storage media). The computer-executable instructions can be part of, for example, a dedicated software application, or a software application that is accessed or downloaded via a web browser or other software application (such as a remote computing application). Such software can be executed, for example, on a single local computer (e.g., with general-purpose and/or specialized processors executing on any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that computer-related aspects of the technology disclosed herein are not limited to any specific computer language or program. For instance, the technology disclosed herein can be implemented by software written in C, C++, Java, or any other suitable programming language. Likewise, the technology disclosed herein is not limited to any particular computer or type of hardware. Certain details of suitable computers and hardware are well-known and need not be set forth in detail in this disclosure.

Furthermore, any of the software-based examples (comprising, for example, computer-executable instructions for causing a computer to assist the performance of any of the methods disclosed herein) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

II. Introduction

A field effect transistor, or FET, as provided herein, comprises a source, a drain, and a conductive channel that can be functionalized with a single active moiety. For example, an enzyme, antibody, aptamer, or other molecule that can be linked to the conductive channel may be used as the single active moiety. Interaction of the active moiety with the appropriate biological substrate results in the change of a local electric field or generation of localized charges, which changes the current flowing through the channel allowing the identification of a biological reaction.

The FET may be a single molecule field effect biosensor. FET bio-sensors may be operated at biologically relevant salt conditions, for example, in the range of about 1 mM to about 100 mM. The Debye screening length of such salt solutions is in the range of about 0.3 nm to about 10 nm, which limits the sensing zone to a few nm outside the surface of the channel and often reduces signal levels to the limit of detectability.

The use of lower salt concentrations during measurement increases the Debye length and enhances the signal. However, reducing salt concentration in some instances is generally not suitable for real-time sensors, where buffer exchange is not possible.

In some examples of the technology disclosed herein, the sensitivity of bioFETs is enhanced by incorporating trap states in the channel of a transistor, and in particular within or in the vicinity of the sensing zone. In other words, the trap state density of the nanostructure is modified for a portion of the nanostructure in proximity (within a distance less than the Debye screening length) with a location where an active moiety is linked to the nanostructure. For every Debye length $L_D$ change in distance, the electric potential of a charge in solution decreases by 1/e. The increased trap states can enhance the observed signal output from the bioFET under biologically-relevant conditions and improves the limit of detection (LOD) of the sensor device.

III. Example Field Effect Sensor Based on a Semiconductor Device

Figure 1B:
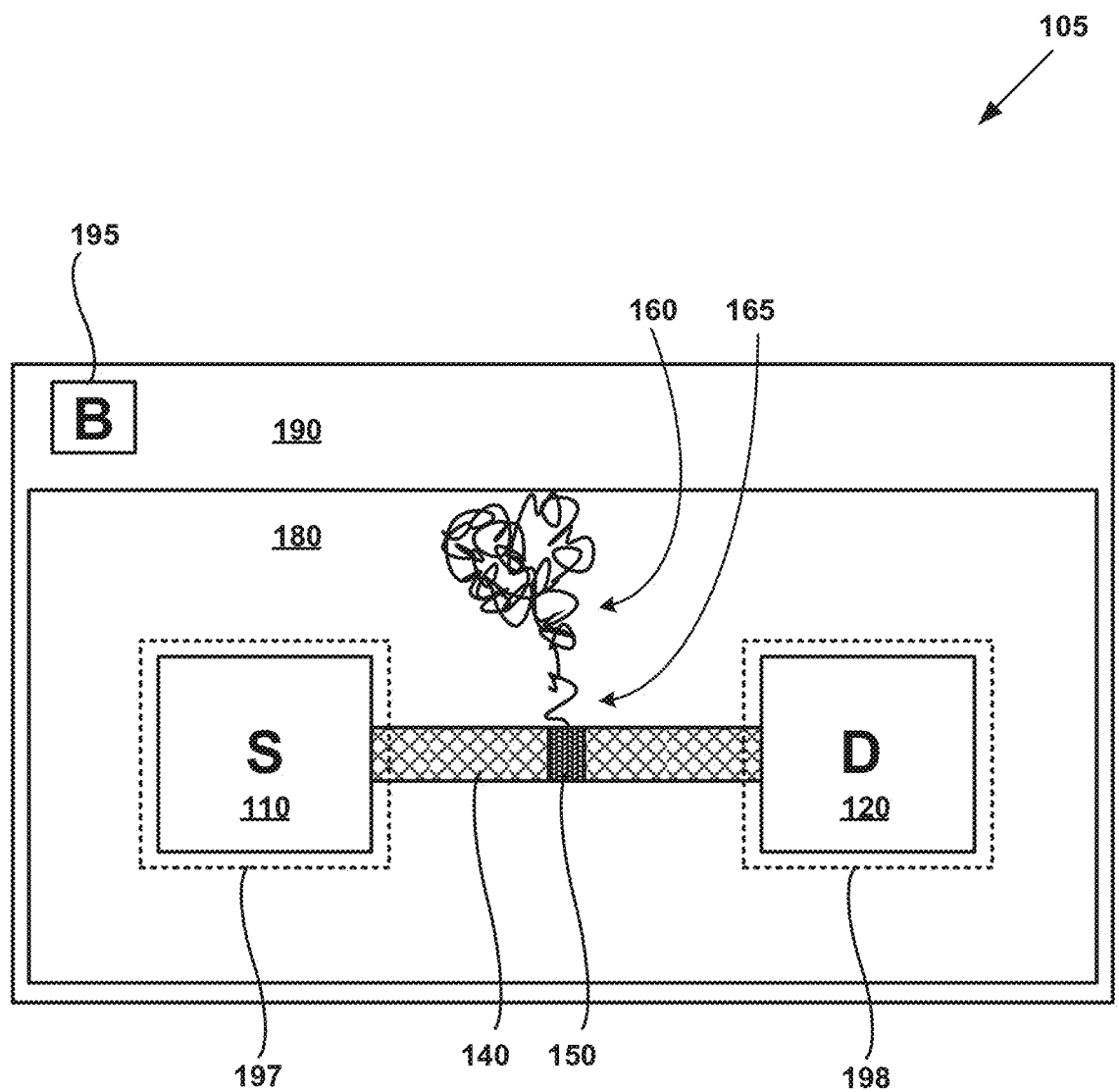

FIGS. 1A and 1B are side view and top view diagrams 100 and 105, respectively, of a semiconductor device as can be manufactured and used according to the technology disclosed herein. The diagrams 100 and 105 show the relative positions of various features, but are not drawn to scale. The semiconductor device includes a source 110, a drain 120, and a gate (e.g., gate terminal) 130. The source 110 and the drain 120 are coupled via a conductive channel implemented with a nanostructure 140. As such, the nanostructure 140 may provide an electrically-conductive channel. The nanostructure 140 can include a semiconductor nanowire (such as a silicon nanowire), a semiconductor nanotube (such as a carbon nanotube or polymer nanotube with semiconductor properties), a semiconductor nanoribbon (such as a graphene or $MoS_2$ nanoribbon), or another semiconductor nanostructure, or a combination of two or more of the above. A portion 150, but not all, of the nanostructure 140 is modified to have an increased trap state density relative to other (e.g., unmodified) portions of the nanostructure 140. The modified portion 150 may be further functionalized with an active moiety, such as sensing moiety 160. One or more sensing moieties 160 are linked to the nanostructure 140 via a linker 165. The linker 165 can be part of the sensing moiety 160 or conjugated to it via appropriate biochemical reactions. For example, a tether, one example of the linker 165, can be used to link one moiety 160 to the modified portion 150 of the nanostructure 140. In some examples, one or more sensing moieties 160 are linked to one or more modified areas (e.g., portion(s) 150) of the nanostructure 140.

In some examples, the semiconductor device is part of an apparatus that further includes a vessel 170 at least partially enclosing the nanostructure 140, the vessel 170 to receive an analyte solution providing electrical communication between the gate terminal and the nanostructure 140. A vessel 170 can be an open or closed container enclosing an analyte solution 175 so that the solution is in contact with the nanostructure 140. As a chemical species 179 (e.g., a nucleotide) of the analyte solution 175 comes in contact with the sensing moiety 160, a change in electrical charge or electric field is induced in the conductive channel of the nanostructure 140. Thus, information about the species 179 of the analyte can be deduced by observing changes in charge or electric field from the FET transistor comprising the source 110, drain 120, and gate 130. As will be discussed further below, because the modified portion 150 of the nanostructure 140 has a different trap state density, this can be advantageously used to increase the signal to noise ratio of the signal generated when the species 179 interacts with the sensing moiety 160.

As shown in FIGS. 1A and 1B, the source 110, the drain 120, and/or the nanostructure 140 is disposed over an insulating layer 180 which comprises, for example, silicon dioxide. The insulating layer 180 in turn is disposed over a substrate, for example, a silicon substrate 190. The silicon substrate 190 can include a body terminal 195 for applying an electrical potential to the substrate 190, which in turn can be used to adjust performance characteristics of the semiconductor device. In an example, the body terminal 195 is coupled to a modulated signal input and the gate terminal 130 is coupled to a fixed voltage (e.g., power or ground). In another example, the gate terminal 130 is coupled to a modulated signal input and the body terminal 195 is coupled to a fixed voltage (e.g., power or ground). In some implementations, the source 110, drain 120, and channel can be fabricated in a bulk semiconductor substrate and isolated from the rest of the circuit via mesa or shallow trench isolation.

Further, as shown in some examples, an insulating material, for example, poly methyl methacrylate (PMMA) can surround the source 110 and drain 120 terminals, and a portion of the nanostructure 140. The insulating enclosures 197 and 198 provide electrical insulation of the source 110 and drain 120, as well as chemical resistance. In some examples, the insulating enclosures 197 and 198 are desirably chemically inert to the analyte solution 175.

In some examples, the modified portion 150 of the nanostructure 140 is generated by the portion being functionalized with the active moiety (e.g., sensing moiety 160), which in turn increases the trap state density in that portion of the nanostructure 140 due to disruptions of the nanostructure's lattice. In some examples, the modified portion 150 of the nanostructure 140 is formed by ion implantation, energetic beam irradiation, plasma exposure, or a combination thereof. In some examples, the modified portion 150 of the nanostructure 140 is formed by ion implantation. In some examples, the modified portion 150 of the nanostructure 140 is formed by diffusion. In some examples, the modified portion 150 of the nanostructure 140 is formed by plasma treatment. In some examples, the modified portion 150 of the nanostructure 140 is formed by energetic beam irradiation, for example an electron or helium (He) ion beam. In some examples, the modified portion 150 is formed by linking an enzyme or an aptamer to the modified portion 150, which disrupts atomic bonds of the nanostructure 140. In some examples, the linked enzyme or aptamer is covalently bound to the modified portion 150 of the nanostructure 140. In some examples, the active moiety (e.g., sensing moiety 160) is a single species of one of the following: a single enzyme, a single antibody, and a single aptamer. In other examples, the active moiety (e.g., sensing moiety 160) includes two or more molecules of an enzyme, an antibody, and/or an aptamer. In some examples, the active moiety (e.g., sensing moiety 160) is part of an antibody, an aptamer, or a polymerase. In some examples, the increased trap state density is desirably in a range of from about $1 \times 10^{12}$ traps/cm$^2$ to about $1 \times 10^{14}$ traps/cm$^2$ (such as any one of: from about $1 \times 10^{12}$ traps/cm$^2$ to about $1 \times 10^{13}$ traps/cm$^2$, from about $1 \times 10^{13}$ traps/cm$^2$ to about $1 \times 10^{14}$ traps/cm$^2$, from about $5 \times 10^{12}$ traps/cm$^2$ to about $5 \times 10^{13}$ traps/cm$^2$, from about $1 \times 10^{12}$ traps/cm$^2$ to about $5 \times 10^{12}$ traps/cm$^2$, from about $5 \times 10^{12}$ traps/cm$^2$ to about $1 \times 10^{13}$ traps/cm$^2$, from about $1 \times 10^{13}$ traps/cm$^2$ to about $5 \times 10^{13}$ traps/cm$^2$, from about $5 \times 10^{13}$ traps/cm$^2$ to about $1 \times 10^{14}$ traps/cm$^2$, from about $2 \times 10^{13}$ traps/cm$^2$ to about $6 \times 10^{13}$ traps/cm$^2$, from about $3 \times 10^{13}$ traps/cm$^2$ to about $7 \times 10^{13}$ traps/cm$^2$, from about $4 \times 10^{13}$ traps/cm$^2$ to about $8 \times 10^{13}$ traps/cm$^2$, from about $5 \times 10^{13}$ traps/cm$^2$ to about $9 \times 10^{13}$ traps/cm$^2$, from about $1 \times 10^{13}$ traps/cm$^2$ to about $2 \times 10^{13}$ traps/cm$^2$, from about $2 \times 10^{13}$ traps/cm$^2$ to about $3 \times 10^{13}$ traps/cm$^2$, from about $3 \times 10^{13}$ traps/cm$^2$ to about $4 \times 10^{13}$ traps/cm$^2$, from about $4 \times 10^{13}$ traps/cm$^2$ to about $5 \times 10^{13}$ traps/cm$^2$, from about $5 \times 10^{13}$ traps/cm$^2$ to about $6 \times 10^{13}$ traps/cm$^2$, from about $6 \times 10^{13}$ traps/cm$^2$ to about $7 \times 10^{13}$ traps/cm$^2$, from about $7 \times 10^{13}$ traps/cm$^2$ to about $8 \times 10^{13}$ traps/cm$^2$, from about $8 \times 10^{13}$ traps/cm$^2$ to about $9 \times 10^{13}$ traps/cm$^2$, and from about $9 \times 10^{13}$ traps/cm$^2$ to about $1 \times 10^{14}$ traps/cm$^2$). In some examples, the increased trap state density is desirably in a range of from about $1 \times 10^{12}$ traps/cm$^2$ to about $1 \times 10^{14}$ traps/cm$^2$ (such as any one of: from about $1 \times 10^{12}$ traps/cm$^2$ to about $1 \times 10^{13}$ traps/cm$^2$, from about $1 \times 10^{13}$ traps/cm$^2$ to about $1 \times 10^{14}$ traps/cm$^2$, from about $5 \times 10^{12}$ traps/cm$^2$ to about $5 \times 10^{13}$ traps/cm$^2$, from about $1 \times 10^{12}$ traps/cm$^2$ to about $5 \times 10^{12}$ traps/cm$^2$, from about $5 \times 10^{12}$ to about $1 \times 10^{13}$ traps/cm$^2$, from about $1 \times 10^{13}$ traps/cm$^2$ to about $5 \times 10^{13}$ traps/cm$^2$, from about $5 \times 10^{13}$ traps/cm$^2$ to about $1 \times 10^{14}$ traps/cm$^2$, from about $2 \times 10^{13}$ traps/cm$^2$ to about $6 \times 10^{13}$ traps/cm$^2$, from about $3 \times 10^{13}$ traps/cm$^2$ to about $7 \times 10^{13}$ traps/cm$^2$, from about $4 \times 10^{13}$ traps/cm$^2$ to about $8 \times 10^{13}$ traps/cm$^2$ traps/cm$^2$, from about $5 \times 10^{13}$ traps/cm$^2$ to about $9 \times 10^{13}$ traps/cm$^2$, from about $1 \times 10^{13}$ traps/cm$^2$ to about $2 \times 10^{13}$ traps/cm$^2$, from about $2 \times 10^{13}$ traps/cm$^2$ to about $3 \times 10^{13}$ traps/cm$^2$, from about $3 \times 10^{13}$ traps/cm$^2$ to about $4 \times 10^{13}$ traps/cm$^2$, from about $4 \times 10^{13}$ traps/cm$^2$ to about $5 \times 10^{13}$ traps/cm$^2$, from about $5 \times 10^{13}$ traps/cm$^2$ to about $6 \times 10^{13}$ traps/cm$^2$, from about $6 \times 10^{13}$ traps/cm$^2$ to about $7 \times 10^{13}$ traps/cm$^2$, from about $7 \times 10^{13}$ traps/cm$^2$ to about $8 \times 10^{13}$ traps/cm$^2$, from about $8 \times 10^{13}$ traps/cm$^2$ to about $9 \times 10^{13}$ traps/cm$^2$, and from about $9 \times 10^{13}$ to about $1 \times 10^{14}$ traps/cm$^2$). In some examples, the increased trap state density is desirably in a range of from about $3 \times 10^{13}$ traps/cm$^2$ to about $4 \times 10^{13}$ traps/cm$^2$ (such as from about $3 \times 10^{13}$ traps/cm$^2$ to about $4 \times 10^{13}$ traps/cm$^2$).

When the semiconductor device is in operation, a voltage difference is applied across the source 110 and drain 120. For example, the source 110 can be held at ground and a higher potential applied to the drain 120, for example, from a power supply or from another transistor, which in turn is coupled to a power supply. The semiconductor device will enter an on state (e.g., a linear or a saturated state of operation) when a voltage applied to the gate 130 exceeds the threshold voltage for the semiconductor device. The threshold voltage is commonly measured between the gate 130 and the source 110. In some examples, a time varying electrical signal (e.g., a voltage-varying signal) is applied to the gate 130, which in turn causes the current flow between the source 110 and drain 120 of the semiconductor device to vary correspondingly. In some examples, a time varying electrical signal (e.g., a voltage-varying signal) is applied to the source 110 or drain 120, which in turn causes the current flow between the source 110 and drain 120 of the semiconductor device to vary correspondingly. As molecules, such as molecule 179, interact with the sensing moiety 160, a small change in the threshold voltage of the semiconductor device is induced. Thus, by observing and measuring changes in the threshold voltage, for example, by observing changes in current flowing through the device or voltage at the drain 120, information about the interacting molecule 179 and the analyte solution 175 can be deduced. In examples where the gate 130 receives a time varying electrical signal, the body terminal 195 may be held at a constant potential, for example, at a ground potential. In other examples, the gate 130 is held at a constant potential and a time varying electrical signal is applied to vary the voltage at the body terminal 195 by observing changes in current flowing through the device or voltage at the drain 120.

While the example of FIGS. 1A and 1B shows a horizontal orientation of the nanostructure 140 relative to the substrate 190, it will be readily apparent to one of ordinary skill in the art having the benefit of the present disclosure that other orientations of the nanostructure 140, for example, vertical orientations relative to the substrate 190, can also be used with the technologies disclosed herein. In vertical orientation nanostructures, trap state densities can be adjusted in a similar fashion as described above, for example, by implanting ions to a portion of the nanostructure 140, by performing localized doping of the nanostructure portion, or by adjusting composition of a source material in a chemical vapor deposition process as the nanostructure 140 is deposited over the substrate 190.

Suitable linkers 165 can be selected depending on the nature of the gate oxide. For SiO$_2$, silanes or other suitable biochemical conjugation molecules can be used. For metal oxide gate materials (such as HfO$_2$ and AlO$_3$), phosphonates, hydroxamates, hydrazine, and combinations thereof, or other suitable biochemical conjugation molecules, can be used. For carbon-based materials, pyrene, anthracene, carboxylate (and combinations thereof), or other suitable biochemical conjugation molecules, can be used. The species of dopant selected is dependent on whether the desired trap states are to be donors, acceptors, or neutral. Appropriate dopant species can be chosen from the chart 1300 discussed below regarding FIG. 13. For example, a carbon (C) implant may create conduction edge states, while an Indium (In) implant may create valence edge states.

IV. Example Semiconductor Device with Modified Trap State Density

In traditional FETs, when one or more dimensions (e.g., length, effective width, or channel length) dimension of the FET is above about 100 nm, the (unavoidable) presence of trap states is manifested in 1/f noise. However, when the dimension of FET is reduced below about 50 nm, the noise spectrum changes dramatically and manifests itself as a bi-stable current level called random telegraph noise (RTN).

Figure 2:
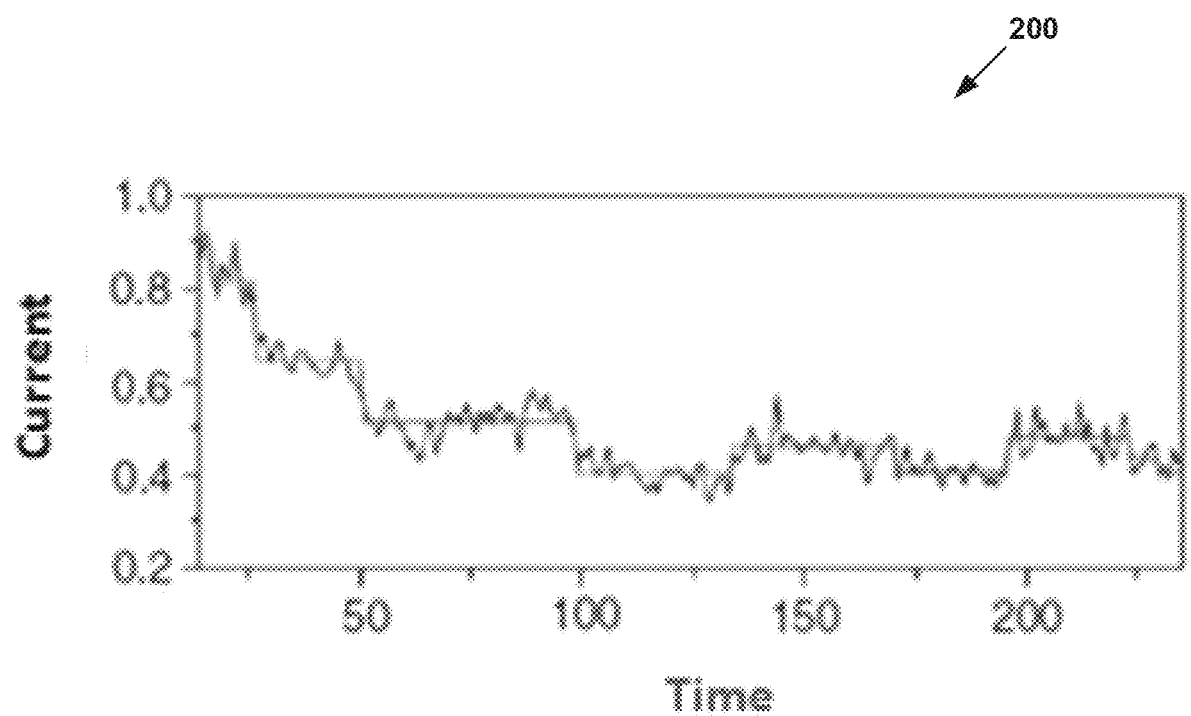
FIG. 2 shows changes in the current flowing through a generalized example field effect sensor in response to biological reactions on its surface.

A chart 200 showing an example of changes in current flow in a functionalized FET is shown in FIG. 2.

Figure 3:
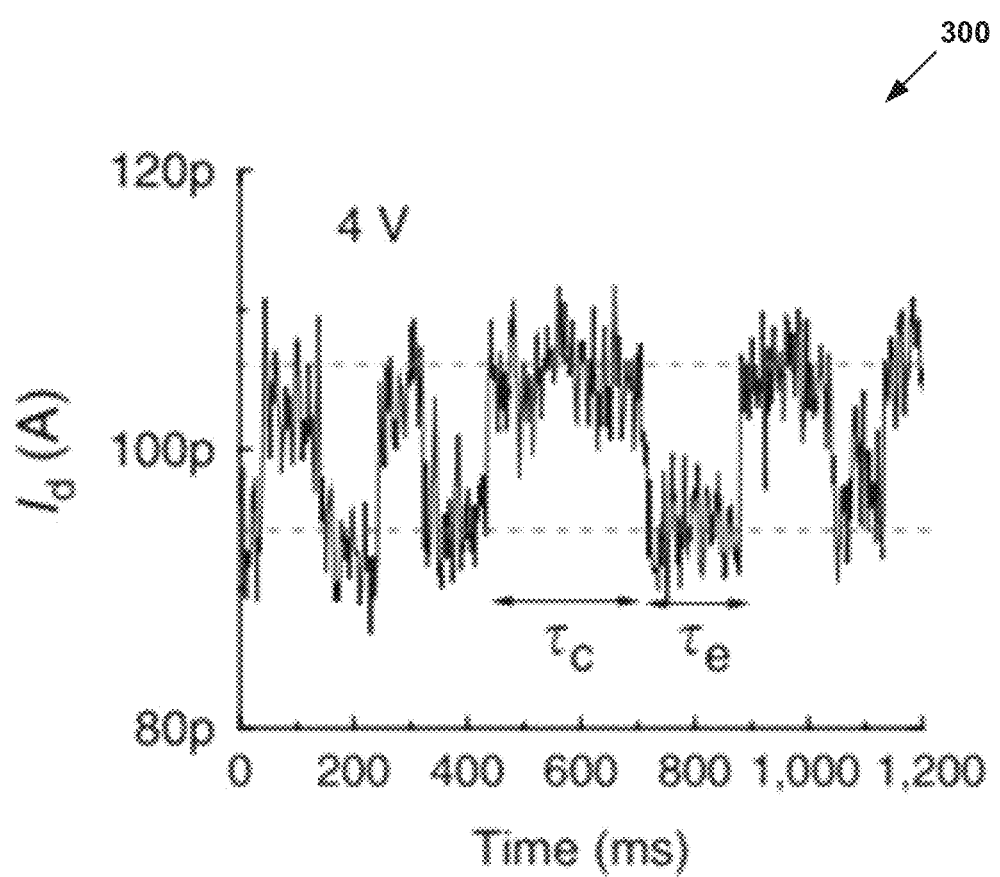
FIG. 3 is an example of random telegraph noise in a 20 nm FET.

A chart 300 of current flow exhibiting RTN in a 20 nm FET is shown in FIG. 3. As shown, the signal is bi-stable and randomly oscillates between two discrete levels.

Figure 4:
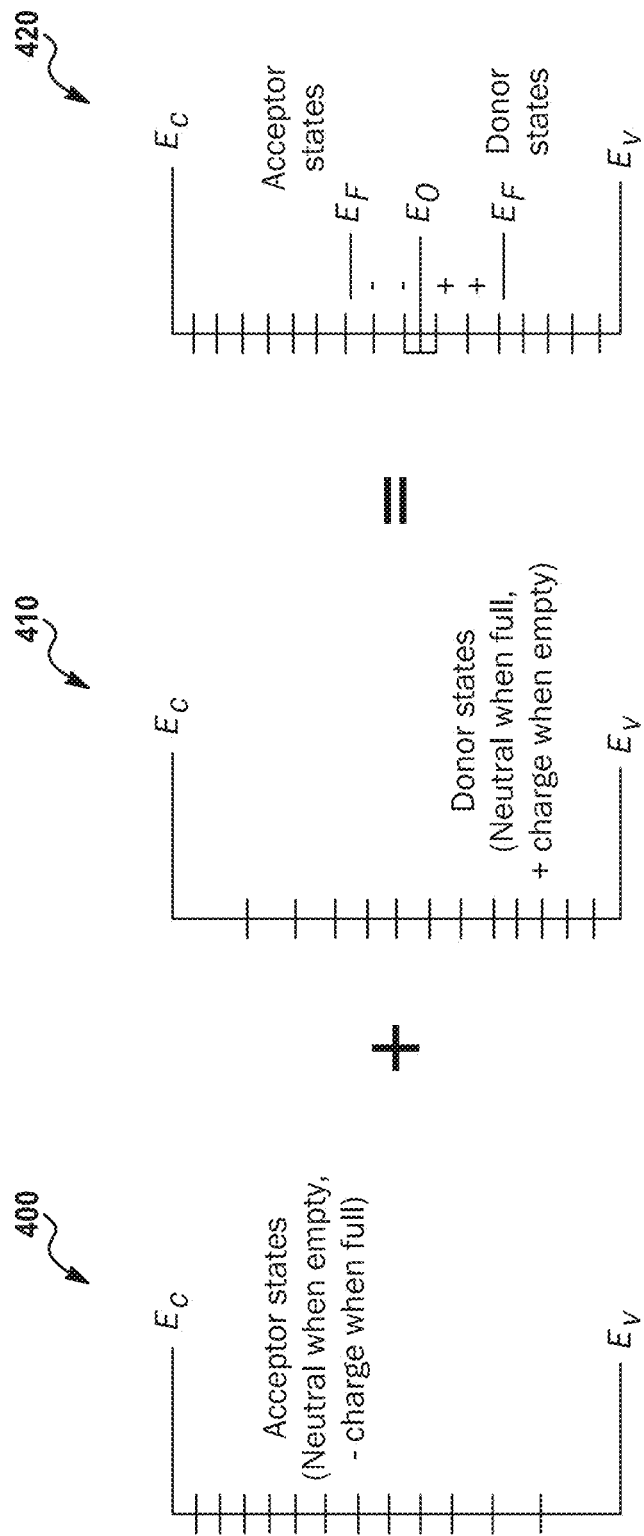
FIG. 4 is a schematic description of energy levels in acceptor traps, donor traps, and mixed traps with a neutral level $E_0$.

The origin of RTN is in the trapping and de-trapping of a single charge carrier within the channel of the FET. FIG. 4 illustrates energy levels that can be occupied by charge carries in a semiconductor material, as can be used in the technology described herein. Traps are generally classified as acceptor traps 400 or donor traps 410. Trap states involve energies larger than the thermal energy of the semiconductor material to ionize and thus tend to not contribute free carriers to the semiconductor material. Thus, trap states in a material tend to restrict charge flow. In the presence of both types of traps, a convenient notation for describing the band structure of the semiconductor is the notion of a neutral level $E_0$. All states above or below $E_0$ are considered to be acceptor or donor states, respectively. When the Fermi level $E_F$ is above or below $E_0$, the net charge of the traps is negative or positive, respectively, as shown in the chart 420.

When voltage is applied to the surface of the semiconductor, for example, from a biochemical reaction that deposits charge near the surface of the sensor, the interface traps (and therefore the neutral level $E_0$) move up or down with the conduction and valence band edges, while the Fermi level $E_F$ remains fixed. This results in a relative change in the offset between $E_F$ and $E_0$ and therefore a change in the fixed charge at the oxide/semiconductor interface, $\Delta C_{ox}$, which in turn shifts the threshold voltage of the transistor as described by Equation 1:

$$V_T = V_{FB} + 2\Delta\varphi_{MS} + \frac{\text{const}}{C_{ox}}.$$

Figure 5:
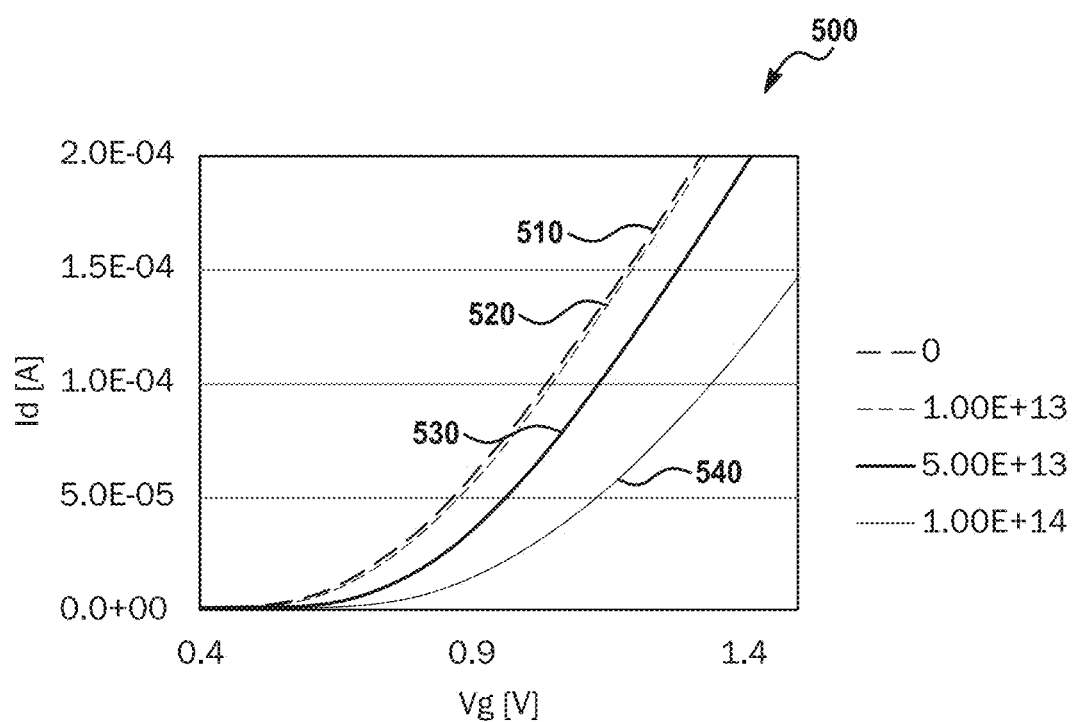
FIG. 5 shows a simulated response of a 20 nm Silicon (Si) nanowire transistor as a function of local trap state density, as can be observed in certain examples of the technology disclosed herein.

This $V_T$ shift is over and above the shift caused by the biochemical reaction. Therefore, based on Equation 1 alone, one would expect that a sensor with trap states to exhibit superior sensitivity. However, trap states are also known to reduce transistor response by degrading the slope on the $I_D V_G$ transfer curve, as shown in the chart 500 illustrated in FIG. 5. The x-axis corresponds to gate-to-source voltage ($V_G$) and the y-axis corresponds to FET drain current ($I_D$). For increasing local trap state densities, the drain current degrades as shown (0.0 trap state density (reference number 510); $1\times10^{13}$ (520); $5\times10^{13}$ (530); and $1\times10^{14}$ (540)).

Figure 6:
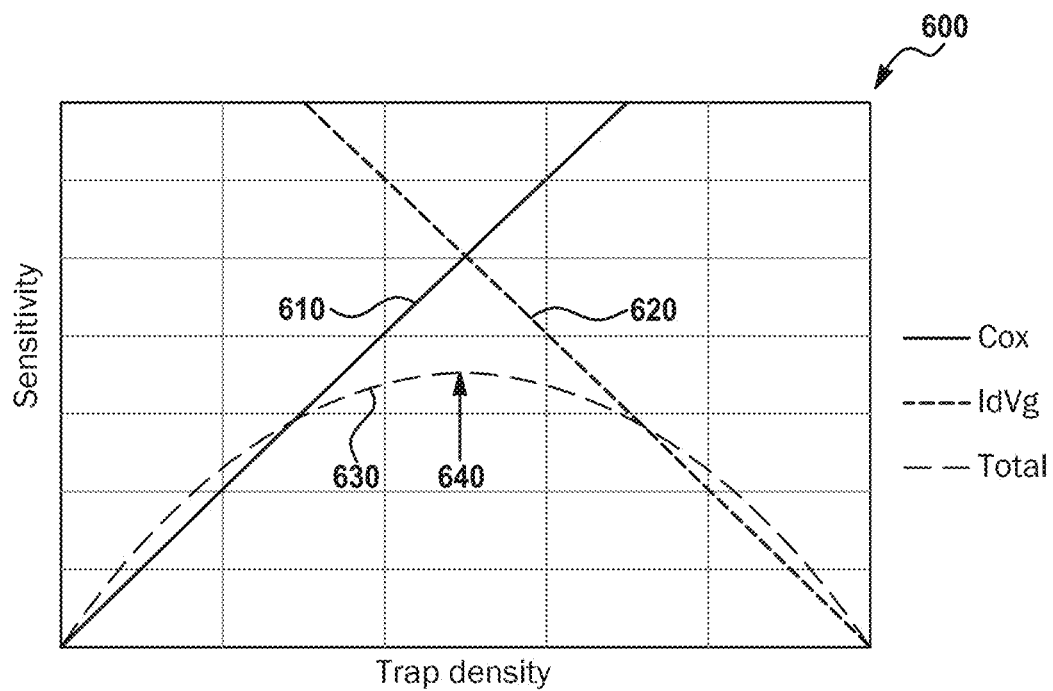
FIG. 6 is an illustration of the competing effects of $\Delta C_{ox}$ modulation and $I_D V_G$ slope degradation, as can be observed in certain examples of the technology disclosed herein.

Since sensor response is directly proportional to $$\frac{\partial I_D}{\partial V_G}$$

and, as shown in the chart 600 of FIG. 6, trap states reduce the slope of the $I_D V_G$ curve, there are two competing effects on sensor sensitivity—improvement due to the additional $\Delta C_{ox}$ modulation, and a degradation due to the reduction of the slope of the $I_D V_G$ curve, resulting in an overall maximum at a certain trap density. The x-axis corresponds to trap density and the y-axis corresponds to FET charge sensitivity in a sensing region. The sensitivity of the FET for increasing $\Delta C_{ox}$ (610) and for the corresponding degradation in drain current $I_D$ (620) is shown. The combined sensitivity based on these two factors (630) is also shown, which exhibits a maximum (640).

As will be readily apparent to one of ordinary skill in the art having the benefit of the present disclosure, localizing the traps in the vicinity of the biochemical reaction being sensed increases the expected improvement in sensitivity, since trap states beyond more than few Debye lengths away from the locale of the biochemical reaction contribute to $I_D V_G$ degradation, but not $\Delta C_{ox}$ modulation.

The expected behavior of a sensor in the presence of trap states can be confirmed with a detailed simulation. An example simulation geometry of a semiconductor device that can be implemented in some examples of the technology disclosed herein is shown in the diagram 700 of FIG. 7. A shown, a 20 nm wide, 100 nm long silicon nanowire (710) with highly doped source/drain regions (720, 725, respectively) and a 2 nm-thick gate oxide is immersed in 10 mM salt solution (730). Sensor response was estimated by computing the difference $\Delta I$ in $I_D V_G$ curves with and without an external charge +2e (740) (where e is the elementary charge of the electron) placed 1 nm away from the surface of the gate oxide. The signal-to-noise ratio (SNR) is computed as $\Delta I/\delta I$, where $\delta I$ is the expected nanowire noise, approximated from the Johnson, shot, and 1/f noise component. The 1/f noise is computed from the Hooge model $S^2(f)=a/Nf$ where a is the Hooge constant ($2.1\times10^{-3}$), N is the number of carriers in the channel, and f is the frequency. A 100 KHz measurement bandwidth was assumed in this example simulation. The trap state density is increased to varying amounts between $10^{12}$ and $10^{14}/cm^2$ in the sensing region 750 shown, which is located between the external charge 740 and the nanowire 710.

Figure 7:
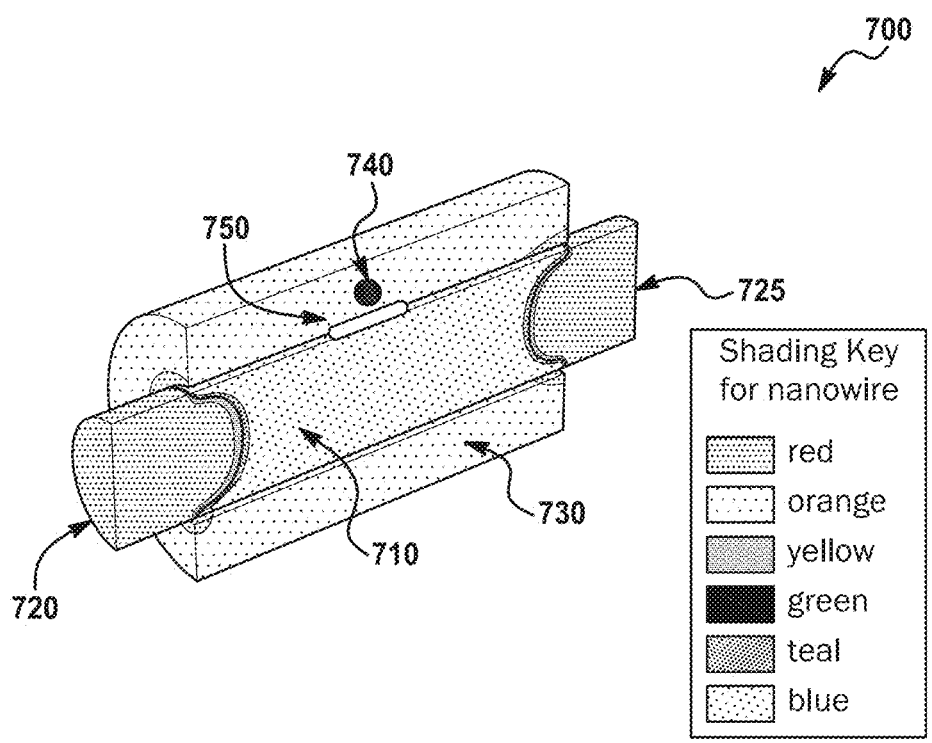
FIG. 7 is a black and white representation of an originally colored diagram illustrating an example of a simulation geometry according to an example of the technology disclosed herein.
Figure 8:
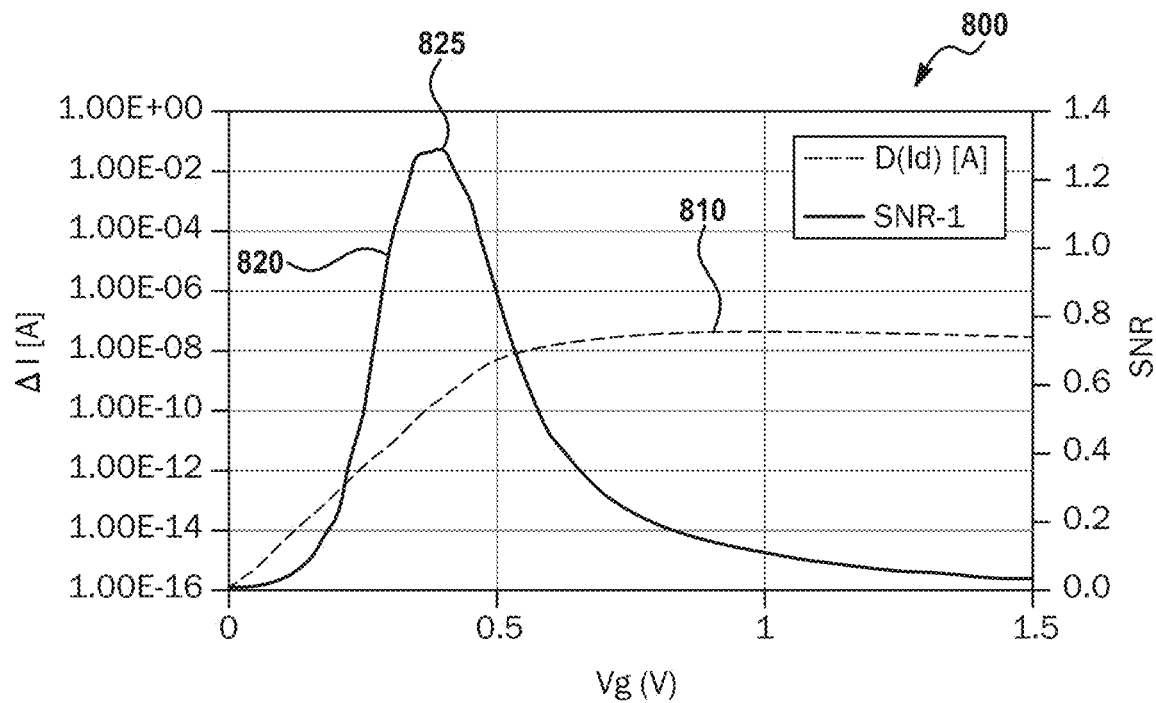
FIG. 8 shows a computed response for a bio-sensor according to an example of the technology disclosed herein.

FIG. 8 is a chart 800 plotting $\Delta I$ as a function of $V_G$ (810) for the sensor depicted in FIG. 7 with a trap density $N_t=10^{12}/cm^2$. The computed SNR ($\Delta I/\delta I$) as a function of $V_G$ is also plotted (820). A strong peak 825 near the point of maximum transconductance $$g_m = \frac{\partial I_D}{\partial V_G}$$

is observed at $V_G$ of ~0.4 V.

Figure 9:
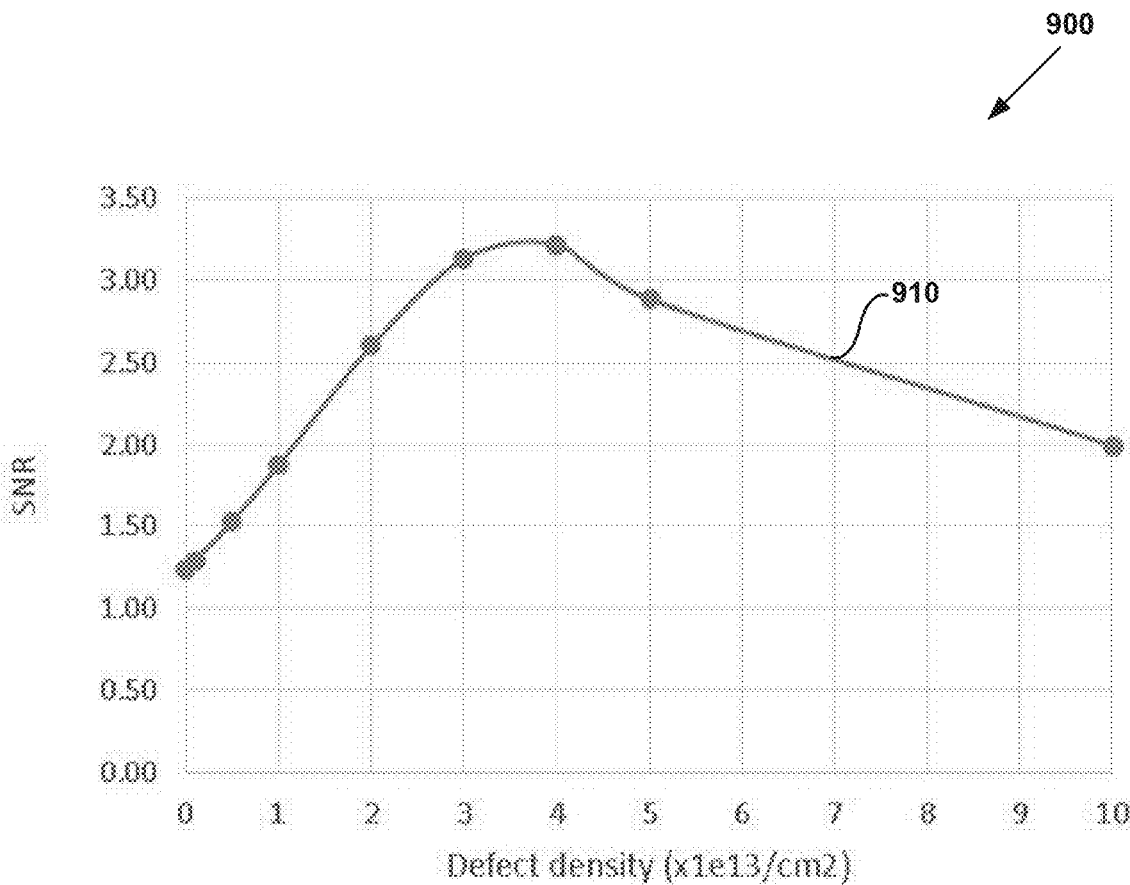
FIG. 9 is a chart plotting computed SNR as a function of trap density according to an example of the technology disclosed herein.

FIG. 9 is a chart 900 with a plot 910 of the peak SNR as a function of $N_t$ for a series of such computations performed for mid-gap states with $N_t=0$-$10^{14}/cm^2$. A peaked response is observed, as expected based on the prior discussion, with nearly 3× improvement in SNR relative to the trap-free case.

It should be noted that the magnitude of SNR improvement and the specific trap density of maximum SNR depend on a large number of factors—details of the transistor design, salinity of the electrolyte, position of the traps states relative to the external charge and the channel/gate oxide interface, position of the trap states relative to the conduction and valence band of the semiconductor, and other relevant factors. While the peak SNR gain may vary, and can be empirically adjusted for factors affecting FET performance (e.g., source doping, channel doping, overlap distance, gate oxide thickness, depth of source, drain, and overlap regions, etc.), the general shape of the response will not. In other words, deliberately introducing appropriately targeted trap states in the sensing zone will generally improve sensor response.

Figure 10:
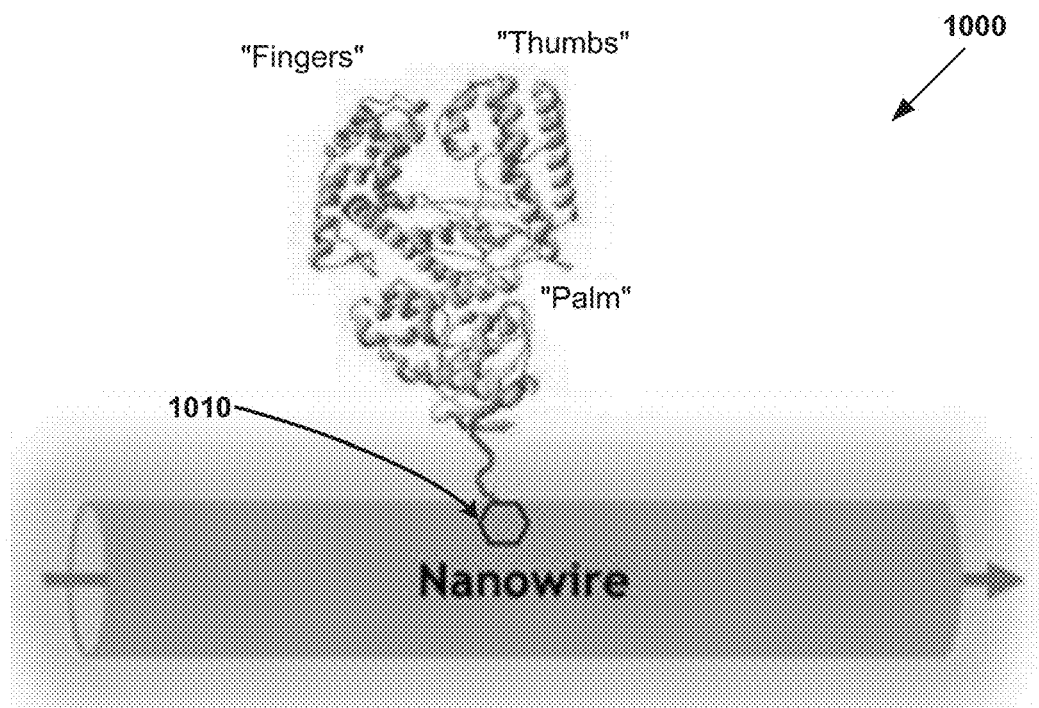
FIG. 10 shows a covalent attachment of the sensing moiety to the surface of the nanowire, as can be performed in certain examples of the technology disclosed herein.

FIG. 10 is a diagram 1000 depicting a covalent attachment of a sensing moiety to the surface of the nanowire. The creation of covalent bonds disrupts the atomic bonds in the vicinity of the attachment site 1010 and creates localized trap states. The selection of linkers 165 used is based on the nature of the surface of the FET sensor. Suitable examples of linkers 165 that can be used include, but are not limited to: silanes for $SiO_2$; phosphonates, hydroamates, and hydrazines for metal oxides such as $HfO_2$; pyrene, anthracene, and carboxylate for carbon-based surfaces or any other number of a multitude of suitable bio-conjugation reactions.

Figure 11:
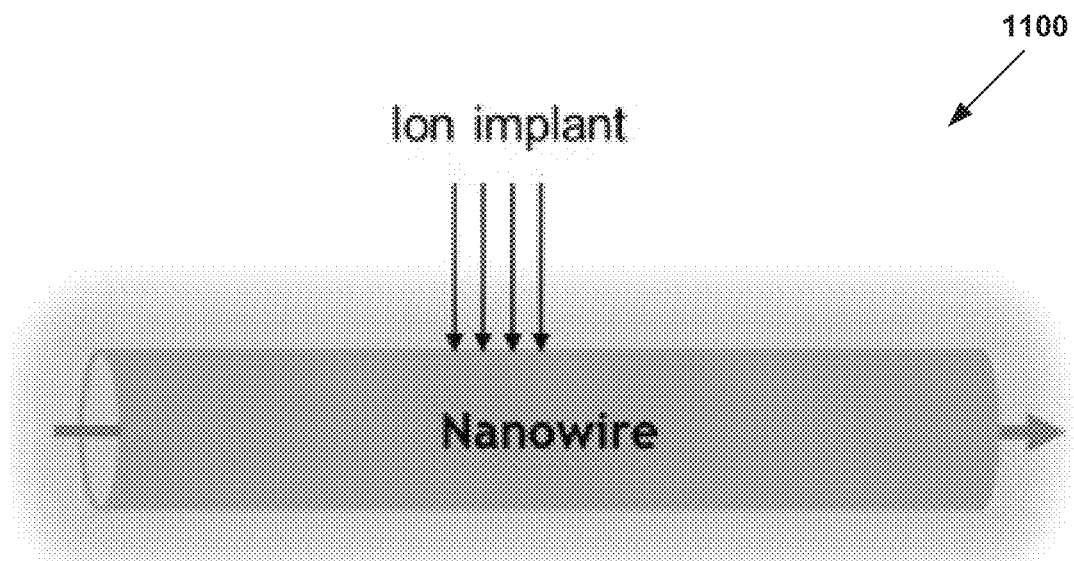
FIG. 11 is an illustration of controlling density and position of trap states as can be performed in certain examples of the technology disclosed herein.

FIG. 11 is a diagram 1100 illustrating that the density and position of the trap states can be controlled top-down with pre-existing semiconductor fabrication techniques or using charged beam irradiation (e.g., electron beam, ion beam, plasma irradiation, or ion implantation of non-doping species).

Figure 12:
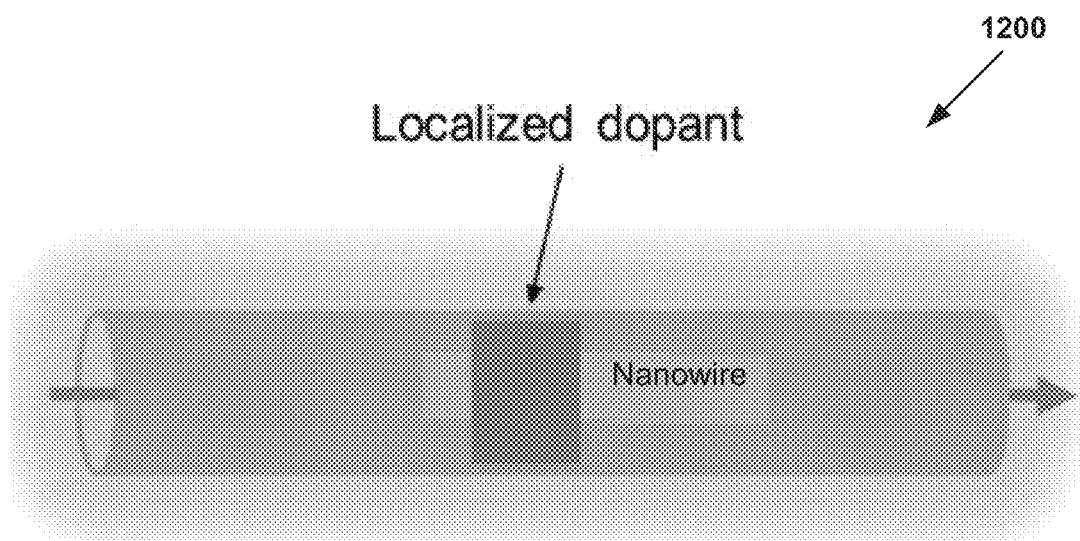
FIG. 12 is a diagram illustrating that the density and position of the trap states can be controlled via localized doping in certain examples of the technology disclosed herein.

FIG. 12 is a diagram 1200 illustrating that the density and position of the trap states can also be controlled via localized doping. For horizontal nanowires, the doping is achieved via implant or diffusion doping. For vertical nanowires the doping also can be controlled during growth.

Figure 13:
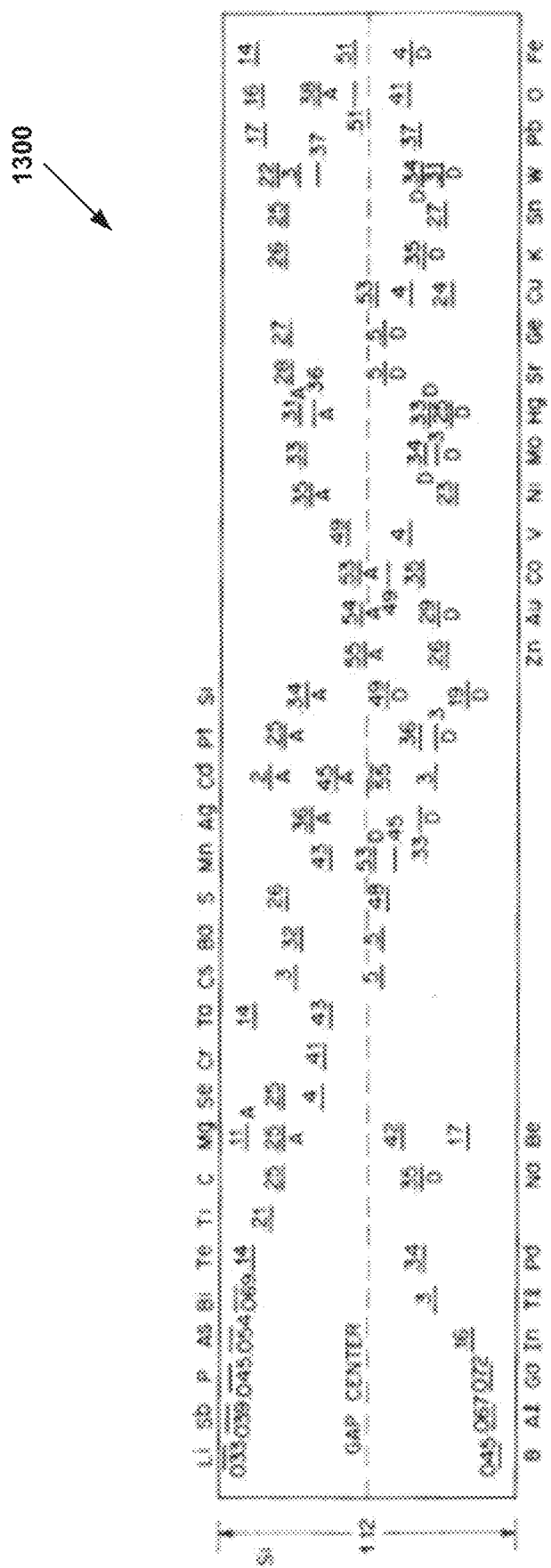
FIG. 13 is a chart showing measured ionization energies for various impurities in Si in one example.

As shown in the chart 1300 of FIG. 13, implant species and dosage can be selected to create traps of the desired type, according to the measured ionization energies for various impurities in Si and subject to other optimization constraints imposed by the selected FET manufacturing technology.

V. Example Use of an Applied Signal Used to Overcome Debye Screening

In one example, from a physics perspective, an ionic solution, such as Na+Cl– or K+Cl–, is indistinguishable from any collection of positive and negative ions, and can be described most generally as a plasma. All plasmas have a characteristic frequency, called "plasma frequency" (PF) above which they become transparent to the applied electrical signal. The plasma frequency is proportional to $m^{-1/2}$ where m is the mass of the charged species. Above the plasma frequency, the electric field changes too fast and the inertia of the charged species does not allow them to move with the electric field and absorb energy from it.

Metals are a common example of targets used to generate a plasma. Metals are completely opaque to visible radiation, but can be transparent to x-rays. Gas plasmas (e.g., Ar+/e–) are opaque up to several hundred kHz but become transparent in the MHz range. Similarly, ionic salt solutions, where the charge carriers are of mass similar to N, Ar can be expected to become transparent in the MHz range.

From a sensing standpoint the transition of an ionic solution from opaque to transparent has an important implication. Below the plasma frequency, electric fields in the solution decay as $\exp(-x/L_D)/x$, where $L_D$ is the Debye length of the plasma. Above the plasma frequency electric fields in the solution delay as $1/x$, a much weaker rate of decay. The ratio of the below/above plasma frequency decay rate is $\exp(-x/L_D)$.

Returning to FIG. 1, the analyte solution 175 that is in contact with the nanostructure can be described generally as a plasma. Such plasmas have a characteristic frequency called a plasma frequency above which they become transparent to the analytes in the solution. By applying an electrical signal above the plasma frequency to the gate 130, the inertia of charged species in the solution prevents them from moving with the electrical field and thus ceases absorbing energy, thereby becoming transparent.

For biological solutions in the range from about 10 mM to about 100 mM, $L_D$ is in the range of from about 0.3 nm to about 3 nm. This may have implications for biosensors operating on the field effect principle, since in many examples the biosensors respond to fields generated within 1 nm to 3 nm of the surface of the sensor. Even then the fields are attenuated before reaching the sensor surface to an extent that limits or negates detection of the corresponding field effect by the sensor. For example, the electric field of a charge 2 nm away from the sensor, immersed in 50 mM solution, will be attenuated ~7x ($e^{-2}$) stronger below the plasma frequency then above it. Thus, the potential for SNR improvement by operating above the plasma frequency is significant.

VI. First Example Circuit for Applying and Measuring Signal of FETs

Figure 14:
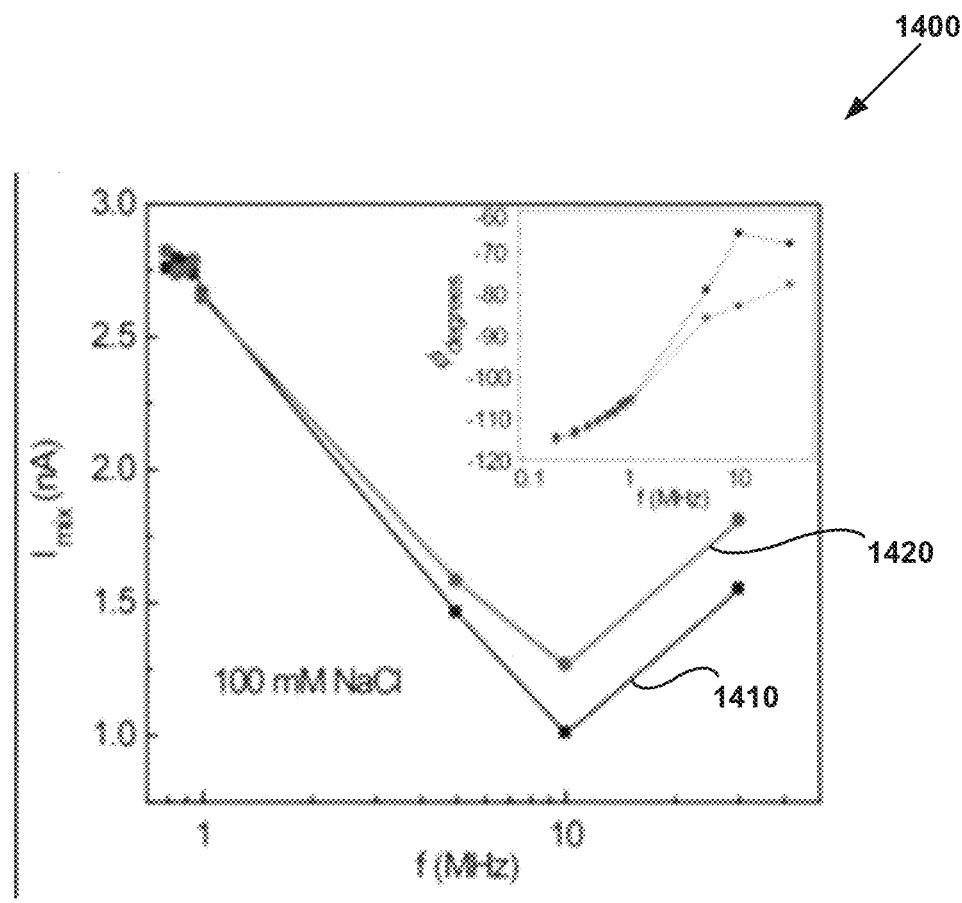
FIG. 14 is a chart showing a response of an example carbon nanotube sensor.

FIG. 14 is a chart 1400 plotting the current $I_D$ of an example field effect sensor (a carbon nanotube) immersed in 100 mM NaCl in the absence (1410) and presence (1420) of a streptavidin/biotin binding on its surface. The chart shows biotin-streptavidin binding on its surface as a function of the measurement frequency. The NaCl concentration is 100 mM, and the Debye length is ~0.3 nm. As shown, due to the strong screening ($L_D$ of ~0.3 nm) the sensor is incapable of detecting the presence of biotin below 2 MHz. In contrast, a clear differential response is observed above 10 MHz, which is above the expected plasma frequency of the NaCl solution.

Figure 15:
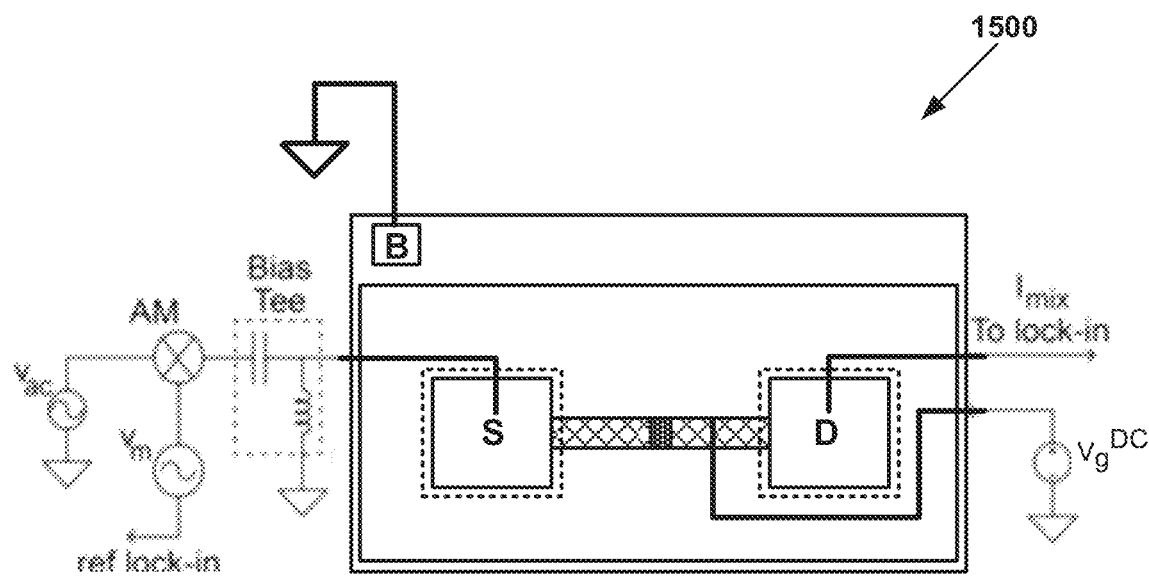
FIG. 15 shows a measurement circuit used for high-frequency detection in certain examples of the technology disclosed herein.

In some examples of the technology disclosed herein, a mixing current measurement circuit 1510 with an amplitude modulated input signal, as illustrated in the diagram 1500 in FIG. 15, can be used to measure $I_D$. However, for larger arrays of sensors (e.g., arrays having hundreds or thousands or more sensors) use of such circuits can become cumbersome and use of such circuits may be infeasible in current process technologies for arrays consisting of millions of sensors.

In addition, there may be at least two issues with detection schemes that use such a mixing current measurement circuit. First, a high-frequency RF signal is fed on a per-sensor basis while controlling the phase shift of the signal. This problem is similar to that of clock distribution in a modern microprocessor. While circuit issues can be addressed through the use of appropriate circuit and design techniques, there is a cost of real estate on the chip that cannot be used for sensing. A second issue is the use of per-pixel lock-in amplification. Lock-in amplifiers are complex circuits that result in drastic overhead in terms of integrated circuit area when implemented.

Figure 16:
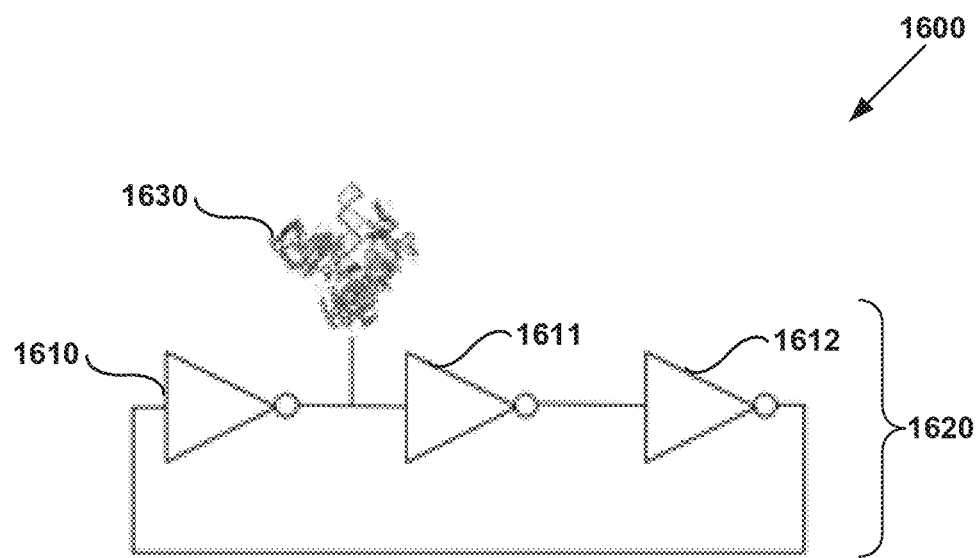
FIG. 16 is a ring oscillator biosensor that can be used in certain examples of the technology disclosed herein.

VII. Second Example Circuit for Applying and Measuring Signal of FETs Disclosed Herein In certain examples of the technology disclosed herein, circuits with voltage-controlled oscillators (VCOs) in a phase-locked loop (PLL) configuration are used for per-sensor generation and detection of the high frequency signal. A schematic illustration 1600 of an example sensor is shown in FIG. 16. An odd number of inverters (three in the illustrated figure: 1610, 1611, and 1612) form a ring oscillator 1620 that resonates at a fixed frequency. A biological reaction, shown in a generalized manner as an enzyme 1630 attached to the gate of one of the transistors in the oscillator inverters, thus provides a variable load to one or more gates of FETs in the ring oscillator, which shifts its resonant frequency. In other examples, more than one enzyme can be attached to a single transistor gate. The oscillating frequency of the ring oscillator (RO) is dependent on the technology used to fabricate the inverters, and the number of inverters in the oscillator. For contemporary complementary metal-oxide-semiconductor (CMOS) fabrication technologies, the resonant frequency of a 3-stage oscillator can be as high as a few GHz. In some examples, more than one inverter stage of the ring oscillator is functionalized with different moieties that produce distinct effects on the oscillation frequency in the presence of a biological reaction—for example one stage may respond by increasing the oscillation frequency of the oscillator, and another may respond by decreasing the oscillation frequency. Such implementations may be particularly desirable in certain examples of multiplexed sensing.

Figure 17:
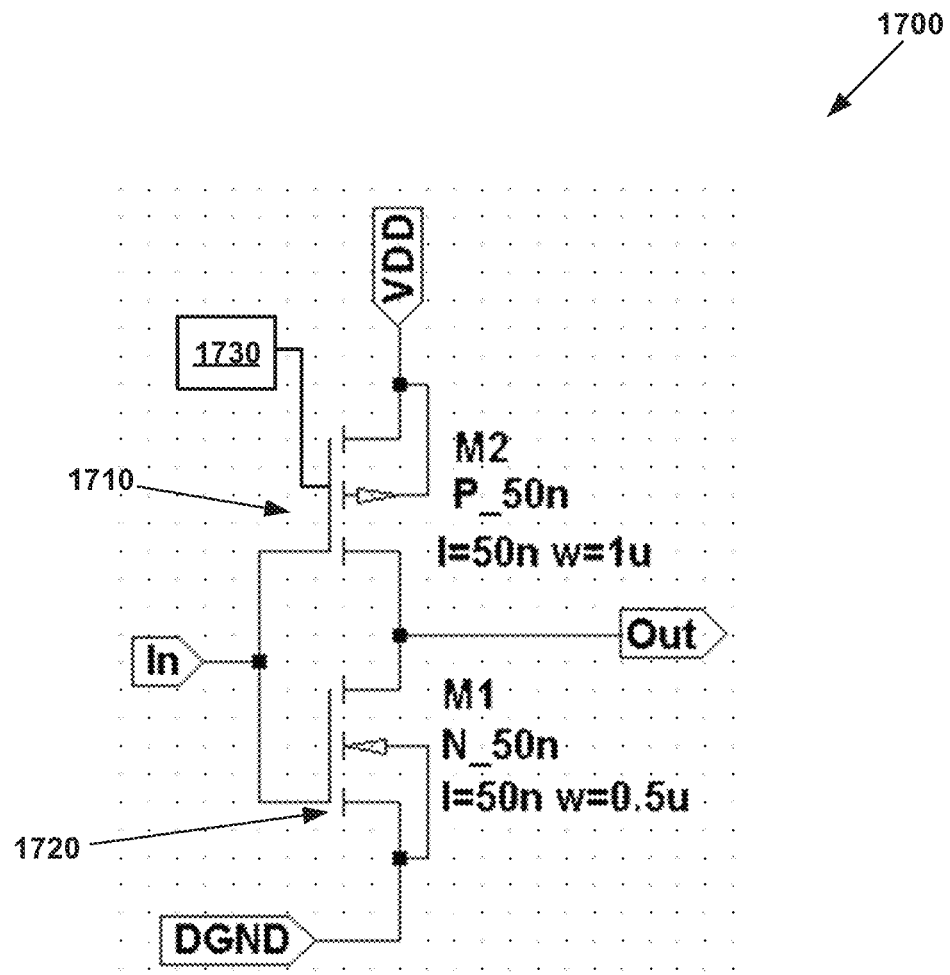
FIG. 17 is a schematic of an inverter used in a ring oscillator according to certain examples of the technology disclosed herein.

An example of a suitable circuit for each of the inverter stages is shown in the schematic 1700 of FIG. 17. Two transistors, one PMOS 1710 and one NMOS 1720, respectively called the pull-up (PU) and pull down (PD) transistors, are connected as shown in FIG. 17. When the signal at the IN port is high, the PU transistor is off while the PD transistor is on, resulting in low potential on the OUT port. Conversely, when the IN signal is low, the PD transistor is off while the PU transistor is on, resulting in high potential on the OUT port. Therefore this circuit inverts the polarity of the input signal, hence the name "inverter."

In some examples of the technology disclosed herein, an enzyme, e.g., a polymerase, will be attached to the gate of either the PU or PD transistor of one of the inverter stages of the RO. The electric field generated either by the enzyme working on its wild-type substrate (e.g., deoxynucleotides (dNTPs), or on a modified substrate (e.g., charge-tag dNTPs, as a non-limiting example), will alter the performance of the particular inverter stage in a time-dependent manner and thus change the resonant frequency of the ring oscillator 1620. In some examples, the FET to which the enzyme is attached can have its local trap state density increased near or at where the enzyme is linked to the nanostructure channel. In the inverter of FIG. 17, an additional component 1730 can be added to model an enzyme linked to the transistor channel near or at a region of increased local trap state density. In this example, the ring oscillator 1620 is therefore behaving as a biologically-driven voltage controlled oscillator (b-VCO). In some examples, only the FET linked to the enzyme has a nanostructure channel, and the other FETs are PMOS or NMOS transistors with a metal or polysilicon gate. In some examples, all of the FETs in the ring oscillator 1620 have nanostructure channels (e.g., a nanotube or nanowire channel). In some examples, only the FET linked to the enzyme is in contact with an analyte solution, while in other examples, one or more or all of the FETs are in contact with the analyte solution.

One efficient way to detect the small changes in resonant frequency of a b-VCO is through a phase-locked loop (PLL). In some examples, the PLL includes two VCOs—one b-VCO whose frequency is controlled by the biological reaction being sensed, and one oscillator that tracks the changes in the b-VCO frequency by adjusting an externally supplied voltage in order to maintain a constant phase difference between its own oscillation and that of the b-VCO. As used herein, this second VCO is dubbed the sense VCO, or s-VCO.

Figure 18:
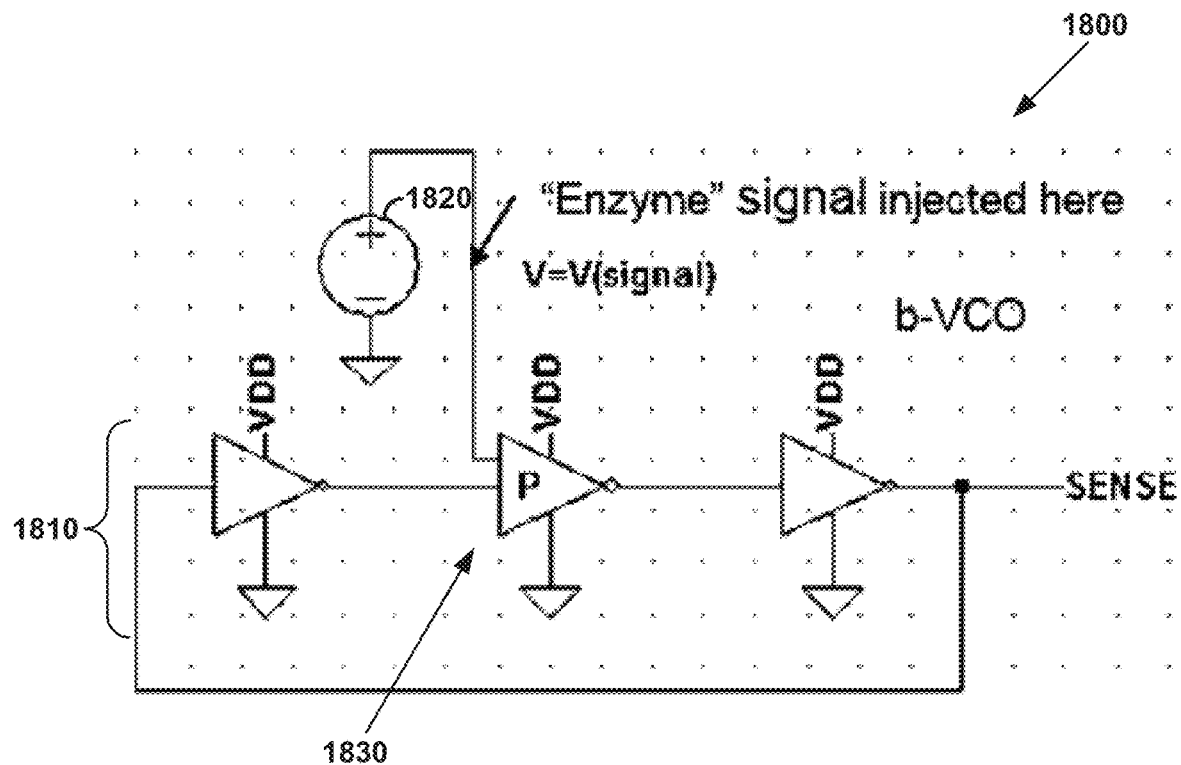
FIG. 18 illustrates a circuit for a biologically-driven voltage controlled oscillator according to certain examples of the technology disclosed herein.

As shown in the schematic 1800 of FIG. 18, the operation of this type of circuit can be confirmed with a SPICE simulation. The b-VCO can be simulated as a ring oscillator 1810 where an external source 1820 supplies a small perturbation on the input of one of the inverter stages 1830, as shown in FIG. 18.

A small voltage $V_{signal}$ from the voltage source 1820 is applied to the input of the second inverter stage 1830 in parallel with the normal signal from the main RO loop. The signal from the b-VCO is tapped at point SENSE and fed to the s-VCO for phase tracking.

Figure 19:
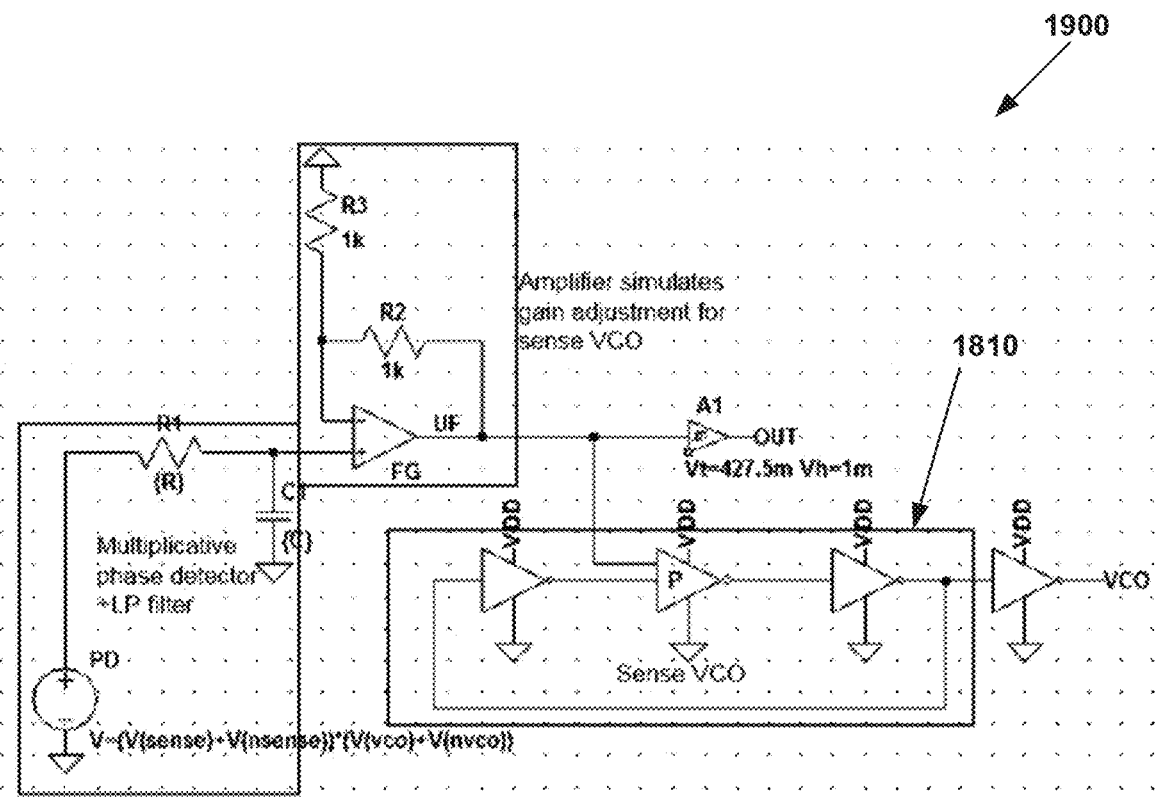
FIG. 19 illustrates a circuit for a sense voltage controlled oscillator and a phase-locked looped, as can be used in certain examples of the technology disclosed herein.

The remainder of the PLL is simulated as shown in the schematic 1900 of FIG. 19. A voltage adder labeled PD adds the outputs of the b-VCO and s-VCO. A low-pass filter comprising the resistors R1 and capacitor C1 converts the high frequency signal to a DC voltage that is proportional to the phase difference between the b-VCO and s-VCO oscillations. The amplifier labeled FG amplifies this DC signal and feeds it back to the s-VCO, thereby providing a feedback loop where the s-VCO frequency adjusts to maintain zero degree offset with the signal from the b-VCO. The output of the amplifier FG is also monitored by a Schmidt trigger A1 that triggers at a set voltage producing, a logic one (1) when the voltage from FG is above a certain level, and logic zero (0) otherwise. It should be noted that the amplifier FG and the Schmidt trigger are added to the simulated circuit for simulations instrumentation and would not necessarily used in an actual implementation. It should also be noted that the PLL circuit implementation described here is an illustrative example and that other circuit implementations may be used, as will be readily understood to those of ordinary skill in the art having the benefit of the present disclosure.

Figure 20:
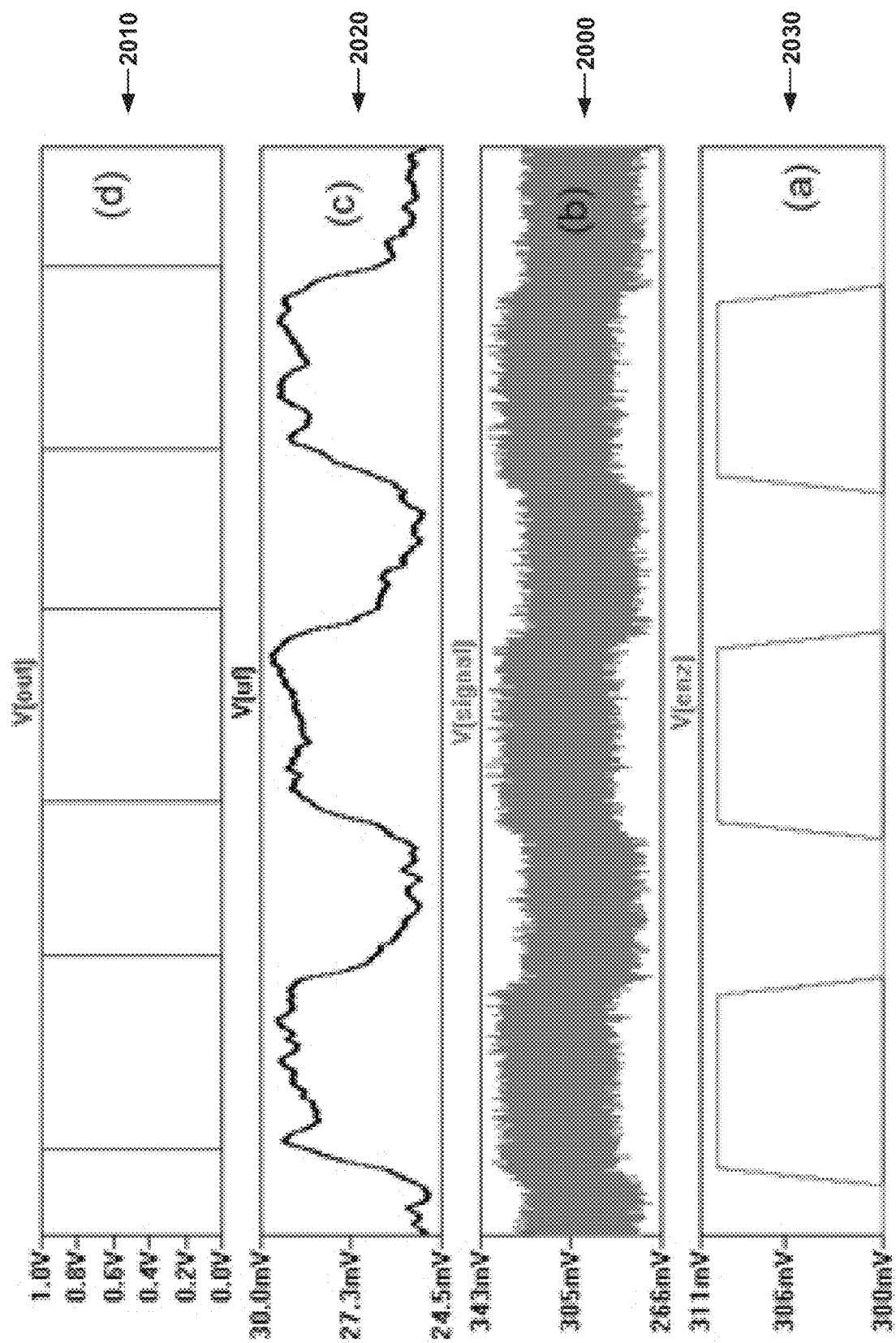
FIG. 20 includes a number of charts for example signals measured at various points in the circuits of FIGS. 17-19.

FIG. 20 includes a number of charts (2000, 2010, 2020, and 2030) showing the voltage signals observed at various points in the circuit illustrated in the schematic 1900 of FIG. 19. The input signal 2000 has a SNR of 0.3 and cannot be called with a single level trigger. The output signal 2010 has SNR>10 and is easily callable with a single-level trigger. The trigger outputs a logic 1 above 28 mV and a logic 0 below that level. An intermediate signal observed at the output of the FG amplifier is also shown in the chart 2020. An idealized response from the enzyme is modeled as the simulated change in voltage output by the PD voltage adder used to model interaction with the sense enzyme is shown in the chart 2030, which is also shown in FIG. 20.

Figure 21:
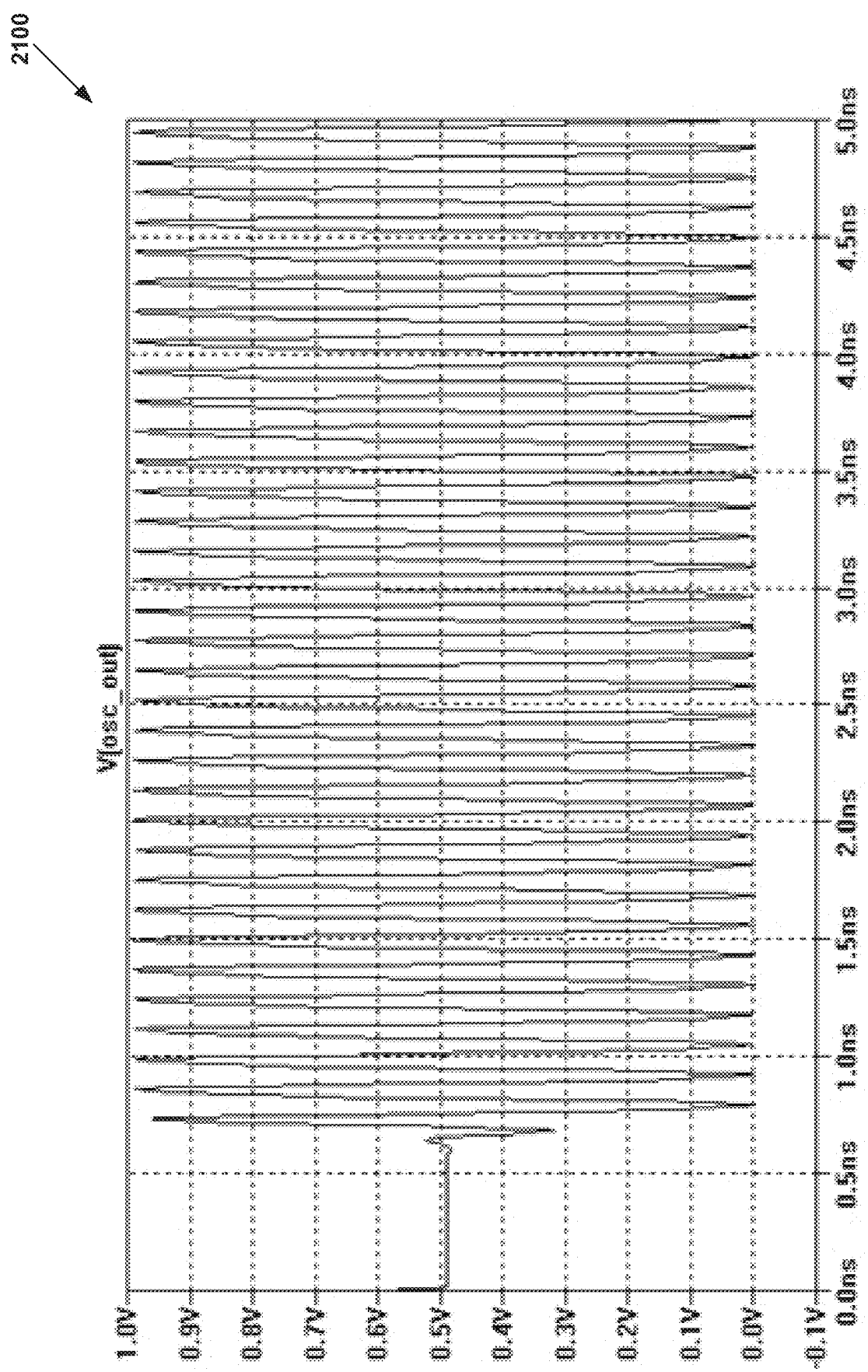
FIG. 21 shows the output of a three-stage ring oscillator as can be used in the certain examples of the technology disclosed herein.

It should be noted that the oscillation frequency of the 3-stage ring oscillators used in this simulation is approximately 6 GHz, as shown in the chart 2100 of FIG. 21. This is well above the plasma frequency of the ionic NaCl solution used, which is around 2 MHz (see FIG. 14). Therefore, enhanced sensitivity for the sensor of FIGS. 1A-1B is demonstrated. The frequency of the example ring oscillator is also well above the bandwidth of the expected signal (approximately 100 kHz-1 MHz), which is so configured in order for the PLL to be able to respond.

In summary, PLLs with b-VCOs can be used for sensing noisy biological signals, particularly at biologically relevant salt concentrations. In some examples, trap state density of a bio-FET used in ring oscillator configurations disclosed herein are used. The circuits can advantageously exhibit lower use of integrate circuit area and be implemented in mature fabrication nodes. For the example of FIGS. 16-20, the two VCOs use a total of 6 transistors, plus an additional 6 to 10 transistors for the phase detector. The output signal of the circuit varies with a frequency ranging from about 10 KHz to about 100 KHz, well below the MHz+ rates used for implementation of the lock-in method. Therefore, the method allows for scale-up of the high-frequency detection scheme to thousands and potentially millions of sensors in a single integrated circuit die.

VIII. Example System Implementation Using Field Effect Sensors Disclosed Herein

Figure 22:
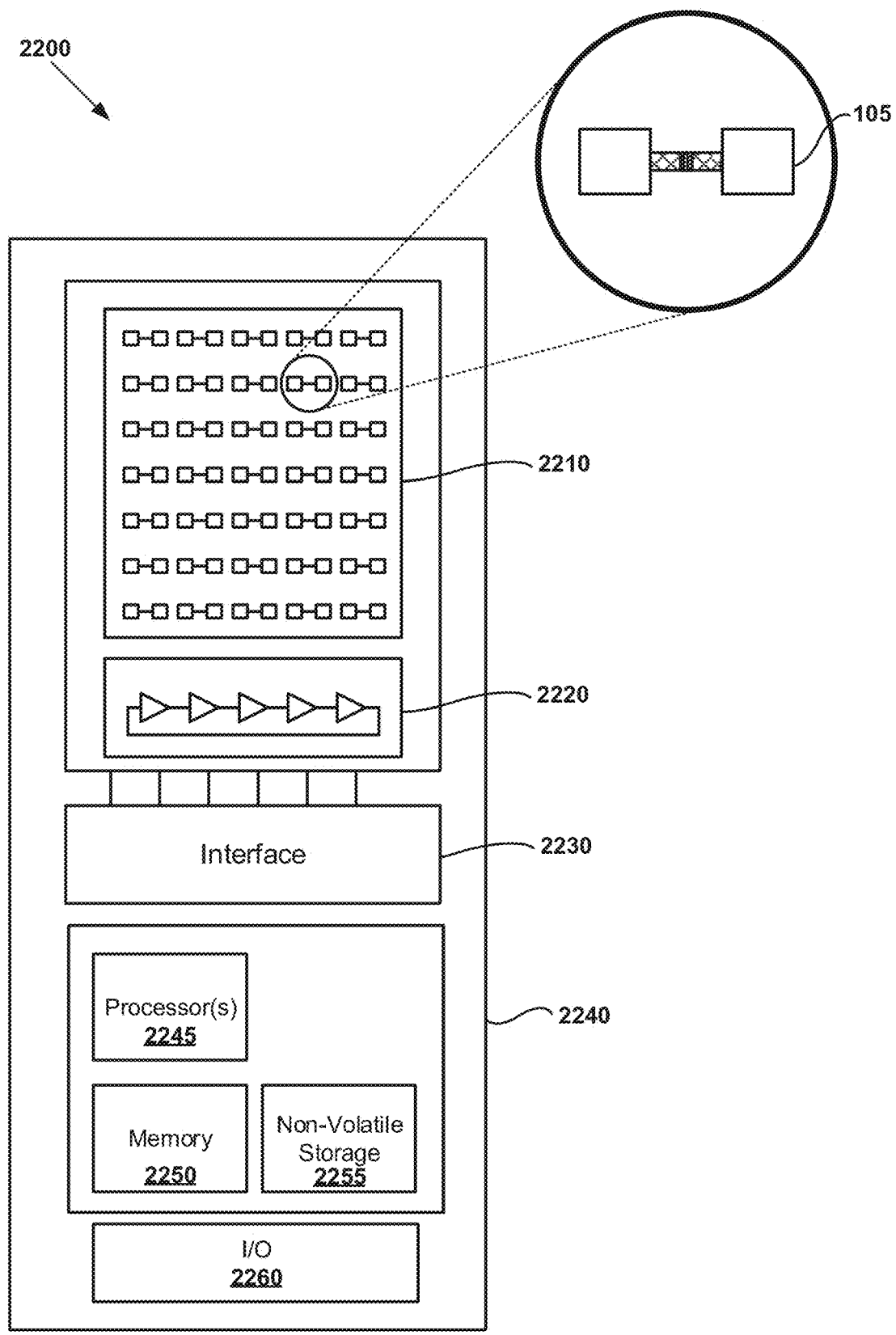
FIG. 22 is a block diagram illustrating an example system that can be used to analyze analyte solutions using FET sensors.

FIG. 22 is a block diagram 2200 illustrating a system that can be used to analyze analyte solutions using FET sensors having enhanced sensitivity due to localized changes in the trap state density, as can be used in certain examples of the technology disclosed herein. As shown, an array 2210 of semiconductor devices have conductive channels with modified trap state densities according to the techniques discussed herein. In some examples, each of the semiconductor devices or groups of devices of the array 2210 has a respective vessel that receives an analyte solution. Such an implementation would be useful for multiplexed measurements on the same chip. In other examples, a vessel may receive an analyte solution and be configured to be a contact with conductive channels of two or more semiconductor devices. Wires leading to and from the terminals of the semiconductor device are coupled to instrumentation circuitry 2220 as described herein. For example, phase detection circuitry including ring oscillator implementations disclosed herein can be coupled to each respective semiconductor device of the array. In some examples, the instrumentation circuitry is implemented on the same substrate as the array. In other examples, all or a portion of the semiconductor circuitry is implemented on a separate integrated circuit that is coupled to the substrate supporting the array. For example, the instrumentation circuitry can be connected to the array via conductive traces on a printed circuit board, within a multi-chip module, or in a multi-die package.

An interface circuit 2230 transmits and receives analog signals to and from the instrumentation circuitry 2220 in order to control operation and to sense electrical changes induced in semiconductor devices of the array. In some examples, the instrumentation circuitry includes a ring oscillator coupled to each of the semiconductor devices implementing a bioFET sensor. In other examples, the instrumentation circuitry 2220 receives output signals from two or more bioFET sensors. The interface in turn can convert the analog signals into a suitable digital encoding for use by one or more processors 2245 within a sequencer computer 2240. The sequencer 2240 can include memory 2250, non-volatile storage 2255, and I/O portions 2260 as well.

IX. Example Method of Manufacturing Semiconductor Devices

Figure 23:
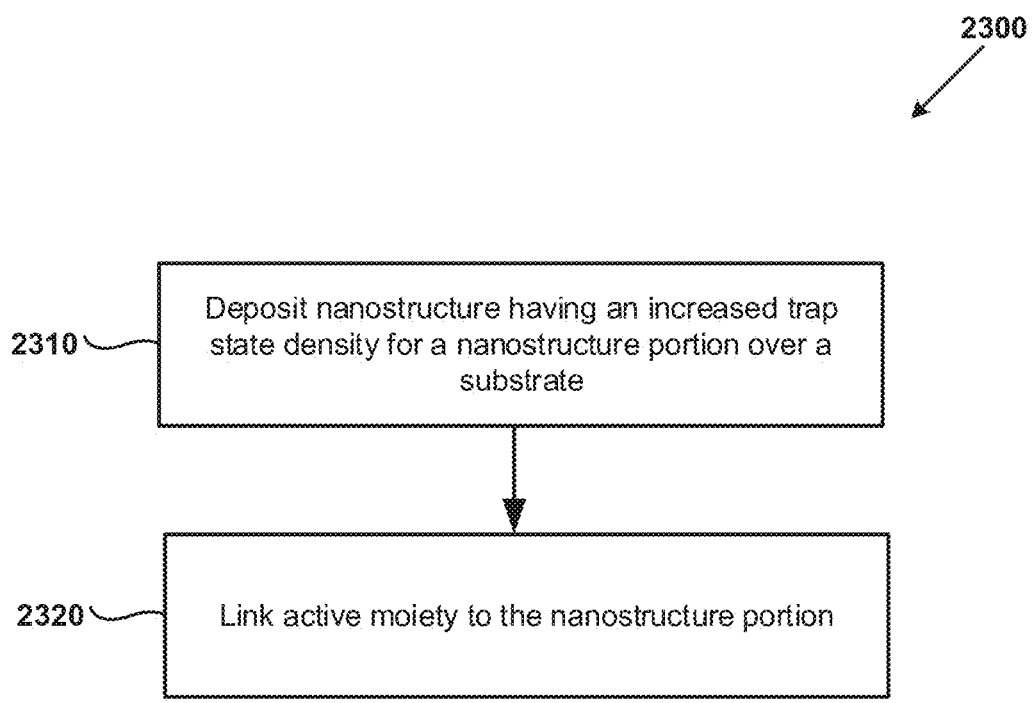
FIG. 23 is a flowchart outlining an example method of manufacturing, as can be performed in certain examples of the technology disclosed herein.

FIG. 23 is a flowchart 2300 outlining an example method of manufacturing, as can be performed in certain examples of the technology disclosed herein. For example, semiconductor devices such as those described above can be manufactured using the illustrated method.

At process block 2310, a nanostructure is deposited over a substrate having at least one source region and at least one drain region within or over the substrate to form an electrically conductive channel between the source region and the drain region. The nanostructure has an adjusted trap state density for a portion, but not all, of the nanostructure. For example, a trap state density can be increased or decreased according to a selected trap state density. In some examples, increased trap state density is induced in the nanostructure by covalently linking an active moiety to a portion of the nanostructure. Thus, the linking of the active moiety creates trap states that are self-aligned to the moiety location. In some examples, trap state density is increased by implanting ions in the nanostructure portion. In some examples, localized doping is performed in order to increase the trap state density of the nanostructure portion. In some examples, trap state density is increased by adjusting a composition of the source material in a chemical vapor deposition process when depositing the nanostructure over the substrate. In some examples, the nanostructure comprises one or more silicon nanowires, graphene nanoribbons, $MoS_2$ nanoribbons, and/or carbon nanotubes.

In some examples of the method, one or more parameters are selected for the semiconductor device. For example, a desired $\Delta C_{ox}$ parameter, a desired drain current to gauge voltage response, or both parameters are selected. A desired trap state density corresponding to the modified parameter(s) for the nanostructure portion is selected. The trap state density can be increased according to the selected trap state density. In some examples, a material and/or dosage is selected according to the desired trap state density.

At process block 2320, an active moiety of a single molecule is linked to the nanostructure portion. For example, the active moiety can be covalently linked to the nanostructure. In some examples, more than one molecule is linked to the nanostructure portion.

X. Example Method of Using Semiconductor Devices

Figure 24:
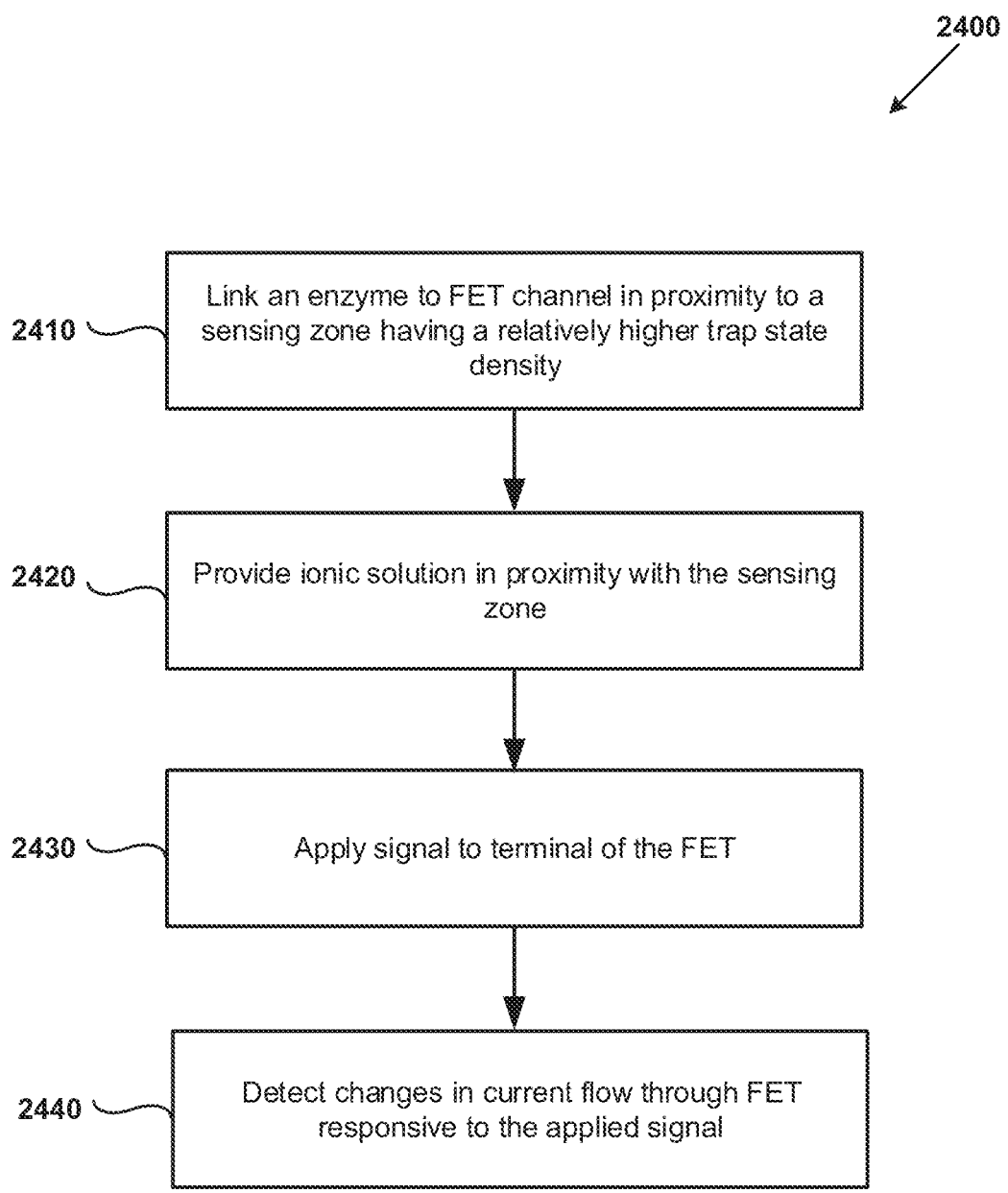
FIG. 24 is a flowchart outlining an example of using a semiconductor device as can be performed according to the technology disclosed herein.

FIG. 24 is a flowchart 2400 outlining an example of using a semiconductor device as can be performed according to the technology disclosed herein. For example, semiconductor devices as discussed above can be used to implement the illustrated method.

At process block 2410, an enzyme is linked to a channel of a field effect transistor in proximity to a sensing zone. The field effect transistor has a source terminal, a drain terminal, and a nanostructure for providing a conductive channel between the source terminal and the drain terminal. A sensing zone includes a region of relatively higher trap state density on the nanostructure.

At process block 2420, an ionic solution is provided in proximity with the sensing zone. For example, the ionic solution can include a salt solution having a selected salinity, and portions of one or more analytes in solution. In some example, the solution has a salinity ranging from about 1 mM to about 500 mM. A vessel can be used to urge the ion solution in contact with the nanostructure, including the sensing zone of the nanostructure.

At process block 2430, a signal is applied to a terminal of the field effect transistor. For example, a time varying signal can be applied to the gate terminal, or the body terminal of the semiconductor device. In some examples, the signal is modulated at a frequency exceeding at least the plasma frequency of the provided ionic solution. For one example, the applied signal is modulated at a frequency exceeding about 1 MHz. For another example, the frequency can exceed substantially 10 MHz. The signal can be applied to a gate terminal or a body terminal of the field effect transistor. For example, the signal is provided to a body terminal field effect transistor, and the gate terminal is held at a fixed voltage. In some examples, the time-varying signal is generated by a biological reaction itself, which is occurring in proximity to the sensing zone. As such, in the examples disclosed herein, the source of the varying signal can be either an externally-applied potential, or a variable charge or electric field produced by the biological reaction itself.

At process block 2440, changes in current flow through the field effect transistor are responsive to the applied signal are detected. The current flow changes are caused by changes in conductivity of the device, which will be observed as molecules and the analyte interact with the linked moiety at the sensing zone. These changes can be detected using, for example, a ring oscillator where at least one inverter of the ring oscillator includes the field effect transistor having the sensing zone. In other examples, different circuits are provided to detect phase changes of an output signal of the field effect transistor relative to the signal applied to the transistor terminal. In some examples, the method further includes sequencing a series of nucleotides in a deoxyribonucleic acid (DNA) or ribonucleic acid (RNA) molecule based on the detected changes. In other examples, the method further includes detecting a nucleotide based on the detected changes.

Some examples of the method may further include providing a ring oscillator circuit having at least one inverter of the ring oscillator including a field effect transistor having a modified sensing zone as disclosed herein.

In some examples of the technology disclosed herein, one or more computer readable storage devices or memory storing computer-readable instructions that when executed by a computer, cause the computer to perform at least any one of the methods disclosed herein. In some examples, a system is configured to perform at least a portion of any one of the methods disclosed herein. In some examples, a system is coupled to computer readable storage devices or memory storing computer-readable instructions that when executed, cause the system to perform at least any one of the methods disclosed herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting.

What is claimed is:

1. A semiconductor device, comprising:
    a source;
    a drain;
    a channel comprising a nanostructure, the nanostructure comprising an unmodified portion and a modified portion including a localized dopant species, the modified portion having an increased trap state density relative to the unmodified portion, and the modified portion being functionalized with an active moiety; and
    a gate terminal in electrical communication with the nanostructure.

2. The semiconductor device of claim 1, wherein the nanostructure comprises at least one of: a nanowire, a nanotube, and a nanoribbon.

3. The semiconductor device of claim 1, wherein the nanostructure comprises at least one of: a silicon nanowire, a carbon nanotube, a polymer nanowire, a graphene nanoribbon, and a $MoS_2$ nanoribbon.

4. The semiconductor device of claim 1, wherein the nanostructure comprises at least one of: graphene, silicene, and phosphorene.

5. The semiconductor device of claim 1, wherein the modified portion is formed by ion implantation, diffusion doping, energetic beam irradiation, plasma exposure, or a combination thereof.

6. The semiconductor device of claim 1, wherein the active moiety comprises an enzyme or an aptamer that is linked to the modified portion of the nanostructure.

7. The semiconductor device of claim 6, wherein the linked enzyme or aptamer is covalently bonded to the modified portion of the nanostructure.

8. The semiconductor device of claim 1, wherein the active moiety is a single molecule of one of the following: a single enzyme, a single antibody, and a single aptamer.

9. The semiconductor device of claim 1, wherein the increased trap state density is in a range of about $1\times10^{-12}$ traps/cm$^2$ to about $1\times10^{-14}$ traps/cm$^2$.

10. An apparatus, comprising:
    the semiconductor device of claim 1; and
    a vessel at least partially enclosing the nanostructure, the vessel to receive an analyte solution providing the electrical communication between the gate terminal and the nanostructure.

11. An apparatus comprising the semiconductor device of claim 1, wherein:
    the semiconductor device further comprises a body terminal coupled to a modulated signal input; and
    the gate terminal is coupled to a fixed voltage.

12. An apparatus comprising a current sensor or ring oscillator, the current sensor or ring oscillator comprising the semiconductor device of claim 1.

13. A method of manufacturing, the method comprising:
    depositing a nanostructure over a substrate having at least one source region and at least one drain region within or over the substrate to form an electrically conductive channel between the source region and the drain region, the nanostructure comprising an unmodified portion and a modified portion including a localized dopant species, the modified portion having an increased trap state density relative to the unmodified portion;
    linking an active moiety to the modified portion; and
    providing a gate terminal in electrical communication with the nanostructure.

14. The method of claim 13, further comprising generating the modified portion having the increased trap state density by implanting ions to a nanostructure portion.

15. The method of claim 13, further comprising generating the modified portion having the increased trap state density by performing localized doping of a nanostructure portion.

16. The method of claim 13, further comprising generating the modified portion having the increasing the trap state density by adjusting a composition of a source material in a chemical vapor deposition process when depositing the nanostructure over the substrate.

17. The method of claim 13, wherein the nanostructure comprises at least one of: a nanowire, a nanotube, and a nanoribbon.

18. The method of claim 13, wherein the nanostructure comprises at least one of: a silicon nanowire, a carbon nanotube, a polymer nanowire, a graphene nanoribbon, and a $MoS_2$ nanoribbon.

19. The method of claim 13, wherein the nanostructure comprises at least one of: graphene, silicene, and phosphorene.

20. The method of claim 13, further comprising:
    selecting: a desired $\Delta C_{ox}$ parameter, or a desired drain current to gate voltage response, or the desired $\Delta C_{ox}$ parameter and the desired drain current to gate voltage response;
    selecting a desired trap state density for the modified portion; and
    increasing the trap state density according to the selected desired trap state density.

21. The method of claim 20, further comprising selecting at least one of a material and a dosage for the modified portion according to the selected desired trap state density.

22. A method of using the semiconductor device of claim 1, comprising:
provide an ionic solution in proximity with the channel;
applying a signal to the gate terminal, or to a body terminal coupled to a modulated signal input while the gate terminal is coupled to a fixed voltage; and
detecting changes in current flow through the channel responsive to the applied signal.

23. The method of claim 22, wherein the signal is modulated at a frequency exceeding a plasma frequency of the solution.

24. The method of claim 22, wherein the solution has a salinity ranging from about 1 millimolar (mM) to about 500 millimolar (mM).

25. The method of claim 22, wherein the detecting of changes in current flow comprises detecting a phase change of an output signal relative to the signal applied to the pate terminal or the body terminal.

26. The method of claim 22, further comprising sequencing a series of nucleotides in a deoxyribonucleic acid (DNA) or ribonucleic acid (RNA) molecule based on the detected changes.

* * * * *

UNITED STATES PATENT AND TRADEMARK OFFICE
CERTIFICATE OF CORRECTION

| | | |
|---|---|---|
| PATENT NO. | : 10,551,342 B2 | Page 1 of 1 |
| APPLICATION NO. | : 16/024299 | |
| DATED | : February 4, 2020 | |
| INVENTOR(S) | : Boyan Boyanov | |

It is certified that error appears in the above-identified patent and that said Letters Patent is hereby corrected as shown below:

In the Claims

Column 21, Line 17, Claim 25, delete "pate" and insert -- gate --, therefor.

Signed and Sealed this
Fifth Day of May, 2020

Andrei Iancu
*Director of the United States Patent and Trademark Office*